United States Patent
Wan et al.

(10) Patent No.: US 11,045,496 B2
(45) Date of Patent: Jun. 29, 2021

(54) ADOPTIVE CELL TRANSFER AND ONCOLYTIC VIRUS COMBINATION THERAPY

(71) Applicant: MCMASTER UNIVERSITY, Hamilton (CA)

(72) Inventors: Yonghong Wan, Ancaster (CA); Scott Walsh, Guelph (CA); Lan Chen, Hamilton (CA); Omar Salem, Mississauga (CA); Boris Simovic, Waterloo (CA)

(73) Assignee: McMaster University, Hamilton (CA)

( * ) Notice: Subject to any disclaimer, the term of this patent is extended or adjusted under 35 U.S.C. 154(b) by 9 days.

(21) Appl. No.: 16/312,897

(22) PCT Filed: Jun. 23, 2017

(86) PCT No.: PCT/CA2017/050772
§ 371 (c)(1),
(2) Date: Dec. 21, 2018

(87) PCT Pub. No.: WO2017/219150
PCT Pub. Date: Dec. 28, 2017

(65) Prior Publication Data
US 2019/0321400 A1  Oct. 24, 2019

Related U.S. Application Data

(60) Provisional application No. 62/354,506, filed on Jun. 24, 2016.

(51) Int. Cl.
| | |
|---|---|
| *A61K 35/17* | (2015.01) |
| *A61P 35/00* | (2006.01) |
| *A61K 39/00* | (2006.01) |
| *C12N 5/0783* | (2010.01) |

(52) U.S. Cl.
CPC .......... *A61K 35/17* (2013.01); *A61K 39/0011* (2013.01); *A61P 35/00* (2018.01); *C12N 5/0636* (2013.01); *A61K 2039/5158* (2013.01); *A61K 2039/5256* (2013.01); *A61K 2039/545* (2013.01); *C12N 2501/2302* (2013.01); *C12N 2501/2315* (2013.01); *C12N 2501/2321* (2013.01); *C12N 2501/999* (2013.01)

(58) Field of Classification Search
None
See application file for complete search history.

(56) References Cited

U.S. PATENT DOCUMENTS

2015/0023938 A1*  1/2015  Yee ................ G01N 33/57492
424/93.71

FOREIGN PATENT DOCUMENTS

| CA | 2951222 A1 | 12/2015 |
|---|---|---|
| WO | 2010105347 A1 | 9/2010 |
| WO | 2017044780 A1 | 3/2017 |

OTHER PUBLICATIONS

Araki et al., Nature, Jul. 2009, 460(2):108-113. (Year: 2009).*
Zeh et al., Mol. Ther., Jan. 2015, 23(1):202-214 (Year: 2015).*
Ramussen et al., Journal of Immunological Methods, 2010, 355:52-60. (Year: 2010).*
Bastin, Donald, et al. "Capitalizing on Cancer Specific Replication: Oncolytic Viruses as a Versatile Platform for the Enhancement of Cancer Immunotherapy Strategies." Biomedicines, vol. 4, No. 3, Paper 21, Aug. 24, 2016.
Bridle, Byram W., et al. "Privileged antigen presentation in splenic B cell follicles maximizes T cell responses in prime-boost vaccination." The Journal of Immunology, p. 1600106, Apr. 27, 2016.
International Search Report and Written Opinion dated Sep. 28, 2017 in International (PCT) Application No. PCT/CA2017/050772 (15 pages).
Rosenberg, Steven A., et al. "Adoptive cell transfer as personalized immunotherapy for human cancer." Science, vol. 348, No. 6230, pp. 62-68, Apr. 3, 3015.
European Patent Application No. 17814390.5, Extended European Search Report dated Feb. 14, 2020.
Fu et al., "An HSV-2 Based Oncolytic Virus Can Function as an Attractant to Guide Migration of Adoptively Transferred T Cells to Tumor Sites," Oncotarget, Nov. 2014, vol. 6(2), pp. 902-914.
International Patent Application No. PCT/CA2017/050772, International Preliminary Report on Patentability dated Dec. 25, 2018.
Klebanoff et al., "Sorting Through Subsets: Which T Cell Populations Mediate Highly Effective Adoptive Immunotherapy?," Journal of Immunotherapy, Nov. 2012, vol. 35 (9), pp. 651-660.

* cited by examiner

*Primary Examiner* — Stacy B Chen
(74) *Attorney, Agent, or Firm* — Borden Ladner Gervais LLP; David Nauman

(57) ABSTRACT

The present invention describes a method for treating cancer comprising adoptive transfer of tumor antigen specific CD8+ T cells and an oncolytic virus vaccine targeting the same antigen.

38 Claims, 12 Drawing Sheets
Specification includes a Sequence Listing.

A

B

C

A

B

A

B

A

B

ADOPTIVE CELL TRANSFER AND ONCOLYTIC VIRUS COMBINATION THERAPY

CROSS-REFERENCE TO RELATED APPLICATIONS

This application claims the benefit of U.S. Provisional Patent Application Ser. No. 62/354,506, filed Jun. 24, 2016, the full disclosure of which is incorporated herein by reference.

FIELD OF THE INVENTION

The present invention relates a combinational immunotherapeutic method for treating cancer.

BACKGROUND OF THE INVENTION

Cancer and conventional cancer therapeutics currently levy a significant socioeconomic burden in terms of emotional/physical distress, lives lost and increased healthcare costs. Conventional therapies show some beneficial clinical outcome but have deleterious side effects that often decrease the patient's quality of life [1]. There is a need for more effective cancer therapies with fewer and less harmful side effects.

It is well appreciated that neoplastic malignancies can be effectively eliminated by the immune system and immunotherapy represents a promising alternative treatment modality for cancer [2].

Immune cells, such as T cells with specificity for tumor-associated antigen (TAA) have the potential to destroy tumors. Such cells can be induced in cancer patients as a result of natural tumor cell turnover or by administering therapeutic vaccines. Unfortunately these cells frequently prove ineffective once infiltrated into the tumor and they often exhibit an exhausted and/or dysfunctional phenotype and lack the cytolytic functions necessary to reduce or destroy the tumor due to tumor-induced local immunosuppression [3-5]. Therefore, the immunosuppressive tumor environment remains a significant obstacle blunting the response induced by conventional cancer immunotherapeutics.

Checkpoint inhibitor based therapies have been used to alleviate suppressive signaling on tumor infiltrating lymphocytes (TILs) and activate an endogenous anti-tumor response [6,7]. Checkpoint inhibitors have shown efficacy in clinical trials but responses are not observed in all treated subjects [8]. Checkpoint inhibitor therapy is reliant on activation of pre-existing TAA specific T cells but in some patients there are not enough pre-existing TAA specific T cells to cause complete tumor regression after therapy induced re-activation [9,10].

Adoptive cell transfer (ACT) of TAA specific T cells represents an excellent alternative to checkpoint inhibitor therapies for treating malignancies (reviewed in [11]). ACT is performed with tumor reactive T cells isolated from cancer patients and grown ex vivo. Once removed from the immunosuppressive environment imposed by the tumor, these cells are activated and proliferated to high numbers before transfer back to the patient. In essence, ex vivo culture converts a low number of dysfunctional T cells with little to no cytolytic activity into billions of fully functional T cells which can effectively home to and destroy cognate tumor cells. Lymphocytes for ACT are derived from an array of sources including peripheral blood mononuclear cells (PBMCs) and TILs. ACT is flexible in that it can utilize lymphocytes that recognize TAAs through their native receptors or lymphocytes can be modified by transduction with a transgene encoding a TAA specific T cell receptor (TCR) or chimeric antigen receptor (CAR) [12,13].

Clinical evidence has shown good anti-tumor efficacy of ACT in non-solid cancers, such as B cell lymphomas. In fact, it has been shown that infusions of human papillomavirus-reactive T cells can also induce regression of HPV-positive metastatic cervical cancer [14]. This strategy is being extended to target non-viral tumor-associated antigens but there are still improvements required to increase tumor infiltration and regression of solid tumors.

Previous work involving ACT has shown that the curative potential of ACT requires the transferred cells to infiltrate the tumor in sufficient quantity and long-term persistence to kill all malignant cells. Clinical evidence suggests that these requirements may be achieved by a high dose of adoptively transferred cells (in the billions) with a minimally differentiated phenotype that maintain replicative capacity [15]. However, these dual goals conflict; generating a high dose of T cells requires extensive in vitro expansion that also results in terminal differentiation and replicative senescence of T cells [16]. Indeed, conventional ACT therapies use terminally differentiated effector T cells and require prior radio- or chemotherapy treatment of the patient to deplete lymphocyte populations and allow better engraftment of the billions of cells that need to be infused [17,18]. In addition, IL2 treatment is required to maintain persistence and activation of the infused cells [19].

Recent studies have shown that less differentiated cells, like central memory T cells, show better success in ACT in terms of persistence of the engrafted cells and clinical outcomes [15, 20]. A method for producing TAA specific central memory T cell culture from PBMC samples has been published [21] but this protocol requires a clinical grade cell sorter, which is labor and resource-intensive, to enrich for the antigen specific cells (also see, U.S. Patent Application Publication No. US 2015/0023938). The present invention provides a method for producing a large ex vivo expansion of antigen specific central memory T cells and an in vivo method for evoking an aggressive cytolytic response from the antigen specific central memory T cells directed to tumor cells expressing the antigen. In combination, these methods constitute an adaptive cell therapy for treatment of cancer that does not require use of a cell sorter or depletion of a subject's endogenous T cell population and thus, represents significant improvement over existing therapies.

SUMMARY OF THE INVENTION

A method to treat cancer in a mammal (e.g. human) is provided comprising adoptive cell transfer and subsequent administration of an oncolytic virus vaccine. In several embodiments, a combination therapy for treating cancer in a subject in need thereof is provided comprising (i) adoptive cell transfer of tumor antigen-specific central memory T (Tcm) cells into the subject followed by (ii) vaccination of the subject with a recombinant oncolytic virus (OV) vaccine expressing the same antigen targeted by the adoptive cell transfer (ACT) T cells to induce cancer destruction and elimination. In preferred embodiments, the ACT T cells are genetically modified to express one or more recombinant T cell receptors (TCR) or chimeric antigen receptor s (CAR) specific for the tumor antigen. In some embodiments, the ACT T cells are autologous T cells derived from the subject to be treated. Preferably, the combination therapy does not comprise a step wherein the subject is immunodepleted.

The methods described herein are useful to treat cancer in a mammal. The term "cancer" as used herein to encompass any cancer, including but not limited to, melanoma, sarcoma, lymphoma, carcinoma, brain cancer (e.g. glioma), breast cancer, liver cancer, lung cancer, kidney cancer, pancreatic cancer, esophageal cancer, stomach cancer, colon cancer, colorectal cancer, bladder cancer, prostate cancer and leukemia. In some aspects, the cancer is a solid tumor. In other aspects, the cancer is a metastasis.

As used herein, the term "mammal" refers to humans as well as non-human mammals and the term "adoptive cell transfer" is meant to encompass infusion of a cell product produced by ex vivo culture of lymphocytes extracted from either peripheral blood or tumor tissue samples.

In one embodiment, a method for generating tumor antigen-specific central memory CD8+ T cells is provided comprising a step of ex vivo cell culture comprising culturing lymphocytes from PBMCs or TILs in the presence of a tumor antigen, an antigen presenting cell such as a dendritic cell, IL21, IL15, and rapamycin and preferably in the absence of IL2. Preferably, CD25+ cells (regulatory T cells and activated T and B cells) are removed from the PBMCs prior to culture. The tumor antigen may, for example be a tumor-associated antigen (TAA), a substance produced in tumor cells that triggers an immune response in a mammal. In some embodiments, the tumor antigen is a self-antigen. In other embodiments, the tumor antigen is a tumor-specific antigen that is unique to the tumor and not expressed in normal cells or expressed in very low amounts in normal cells (e.g. neo-antigen).

In related embodiments, the tumor antigen is a tissue-specific tumor antigen with higher expression in cancer cells compared with normal cells, non-limiting examples of which include tyrosinase, MART-1, gp100, TRP-1/gp75 and TRP-2 proteins. In other embodiments, the tumor antigen is a tumor-specific and shared antigen that is expressed in cancer and testis but not expressed or expressed in very small quantities in other normal tissues (cancer-testis or CT antigens), non-limiting examples of which include BAGE, CAMEL, MAGE-A1 and NY-ESO-1. In other embodiments, the tumor antigen is a tumor-specific and unique antigen (neoantigen) that is expressed only in tumor cells non-limiting examples of which include CDK4, catenin, caspase-8, MUM-1, MUM-2, MUM-3, MART-2, OS-9, p14ARF, GAS7, GAPDH, SIRT2, GPNMB, SNRP116, RBAF600, SNRPD1, PRDX5, CLPP, PPP1R3B, EF2, ACTN4, ME1, NF-YC, HLA-A2, HSP70-2 and KIAA1440. In other embodiments, the tumor antigen is an overexpressed tumor antigen that is overexpressed in cancer cells compared with normal cells. Examples of tumor-associated antigens include oncofetal antigens such as alphafetoprotein (AFP) and carcinoembryonic antigen (CEA), surface glycoproteins such as CA 125, oncogenes such as Her2, melanoma-associated antigens such as dopachrome tautomerase (DCT), GP100 and MART1, cancer-testes antigens such as the MAGE proteins and NY-ESO1, viral oncogenes such as HPV E6 and E7, proteins ectopically expressed in tumors that are usually restricted to embryonic or extraembryonic tissues such as PLAC1. As one of skill in the art will appreciate, an antigen may be selected based on the type of cancer to be treated using the present method as one or more antigens may be particularly suited for use in the treatment of certain cancers. For example, for the treatment of melanoma, a melanoma-associated antigen such as DCT may be used.

In some preferred embodiments, to generate tumor antigen (e.g. TAA) specific CD8+ T cells, the present method includes a step wherein the ex vivo cultured cells (e.g. autologous PBMCs obtained from a subject or PBMCs having a histocompatible phenotype to a subject) are genetically modified to express one or more recombinant TCR(s)) or CAR(s) to confer tumor antigen specificity. The transduced cells are cultured ex vivo in the presence of a tumor antigen, an antigen presenting cell such as a dendritic cell, IL21, IL15, and rapamycin. CAR is a fusion protein composed of an antibody derived extracellular single-chain variable fragment (scFv) with an antigen recognition moeity and an intracellular T-cell activation domain. Recombinant TCRs comprise an alpha chain and a beta chain and may e.g. recognize HLA-A2/peptide complexes. The cells may be transduced with a vector, e.g. a lentiviral or retroviral vector, carrying a transgene cassette supporting expression of the selected TCR/CAR. Methods of introducing the transgene cassette into the vector are well known to those of ordinary skill in the art. Generally, the vector is modified to express the TCR/CAR. In this regard, a nucleic acid sequence encoding the selected TCR/CAR is incorporated into the selected vector using well-established recombinant technology. In some embodiments, the TCR or CAR is specific for MART-1, gp100, NY-ESO-1, or a member of the MAGE family, (e.g. MAGE-A3). Advantageously, tumor antigen (e.g. TAA) specific CD8+ T cells generated by the methods described herein do not require purification (or further enrichment), e.g. using tetramer labeling and a clinical grade sorter prior to expansion (e.g. rapid expansion with anti-CD3 and antiCD28 antibodies and IL2). Thus, in preferred embodiments, a method for adoptive cell transfer is provided comprising (i) culturing PBMCs or TILs obtained from a subject with cancer in the presence of tumor antigen-loaded antigen presenting cells (APCs, e.g. autologous dendritic cells), IL21, IL15, and rapamycin and preferably in the absence of IL2 to create a cell population enriched for tumor antigen specific CD8+ T cells, (ii) expanding the tumor antigen specific CD8+ T cells with anti-CD3 and anti-CD28 antibodies and IL2 and (iii) reintroducing the cells into the subject, wherein the method does not comprise performance of a step to purify (or further enrich) T cells between steps (i) and (ii), such as sorting tetramer$^+$ cells.

In preferred embodiments, lymphocytes from PBMCs or TILs are cultured ex vivo in the presence of tumor antigen, APCs, IL21, IL15, and rapamcyin for about 1 to about 4 weeks, e.g. for about one week, for about two weeks, for about three weeks, for about four weeks or any range there between in the presence of a tumor antigen, antigen presenting cells such as a dendritic cells, IL21, IL15, and rapamycin and preferably in the absence of IL2, which may be followed by about one to about two weeks, about one week or about two weeks in the presence of IL21, IL15 and rapamycin in the absence of the tumor antigen and antigen presenting cells. In a particularly preferred embodiment, lymphocytes from PBMCs are cultured ex vivo for about 2 weeks in the presence of tumor antigen peptide-loaded dendritic cells, IL21, IL15 and rapamycin and for about 1 week in the presence of IL21, IL15 and rapamycin and in the absence of tumor antigen peptide-loaded dendritic cells. Advantageously, tumor antigen specific CD8+ T cells produced according to the methods herein described can be introduced into a mammal without the need for lymphodepletion and without the need for administering IL-2 to the subject. Thus, in some embodiments, a method for adoptive cell transfer is provided comprising (i) culturing lymphocytes from PBMCs or TILs ex vivo in the presence of a tumor antigen, an antigen presenting cell such as a dendritic cell, IL21, IL15, and rapamycin and (ii) administering the resulting tumor antigen (e.g. TAA) specific CD8+ T cells to a mammal without destruction of existing lymphocytes in the mammal(lymphodepletion or lymphoablation) by chemotherapeutic or radiologic means and without administering IL-2 to the subject.

According to the combination therapy described herein, an oncolytic virus expressing the tumor antigen is administered to the subject following adoptive transfer of the tumor antigen specific CD8+ T cells. Adoptive transfer of the tumor antigen specific CD8+ T cells may be accomplished by any suitable method including the methods described herein and the methods described in U.S. Patent Application Publication No. US 2015/0023938, the contents of which are incorporated herein by reference.

In some embodiments, the combination therapy comprises (i) culturing TILS from a subject with a tumor ex vivo in the presence of antigen presenting cells (APCs) loaded with tumor antigen peptide and IL21, expanding the cells in culture and reintroducing them into the subject and (ii) administering an oncolytic virus expressing the same tumor antigen to the subject.

In other embodiments, the combination therapy comprises (i) culturing TILS from a subject with a tumor ex vivo in the presence of APCs loaded with tumor antigen peptide and IL21, IL15 and rapamcyin, expanding the cells in culture and reintroducing them into the subject and (ii) administering an oncolytic virus expressing the same tumor antigen to the subject.

In other embodiments, the combination therapy comprises (i) culturing PBMCs from a subject ex vivo in the presence of APCs loaded with tumor antigen peptide and IL21, expanding the cells in culture and reintroducing them into the subject and (ii) administering an oncolytic virus expressing the same tumor antigen to the subject.

In other embodiments, the combination therapy comprises (i) culturing PBMCs from a subject ex vivo in the presence of APCs loaded with tumor antigen peptide and IL21, IL15 and rapamycin, expanding the cells in culture and reintroducing them into the subject and (ii) administering an oncolytic virus expressing the same tumor antigen to the subject.

In related embodiments, the PBMCs are transduced with a recombinant TCR or CAR specific for the tumor antigen prior to ex vivo culture.

In some embodiments, the oncolytic virus expressing the tumor antigen is administered to the mammal about 8 to 72 hours after the tumor antigen specific CD8+ T cells are transferred. In preferred embodiments, the oncolytic virus expressing the tumor antigen is administered to the subject about 12 to 48 hours, about 20 to 28 hours, or about 24 hours after the tumor antigen specific CD8+ T cells are transferred.

Any replication-competent oncolytic virus expressing a tumor antigen may be administered according to the combination therapy herein described. In some preferred embodiments, the replicative oncolytic virus is a rhabdovirus such as a VSV or a Maraba rhabdovirus that preferably comprises one or more genetic modifications to increase selectivity of the virus for cancer cells.

The replicative oncolytic virus vaccine may be administered by one or more of a number of routes. In some embodiments, the replicative oncolytic virus is a rhabdovirus and is administered to the mammal by the intravenous route. In other embodiments, the replicative oncolytic virus is a vaccinia virus and is administered to the mammal intravenously (IV), intramuscularly (IM), intraperitoneally (IP), or intratumorally (IT). As will be appreciated by one of skill in the art, the replicative oncolytic virus (e.g. rhabdovirus or vaccinia virus) will be administered in a suitable carrier, such as saline or other pharmaceutically suitable buffer.

BRIEF DESCRIPTION OF THE DRAWINGS

Embodiments of the invention are shown in more depth by the following descriptions to their respective drawings listed below.

DEFINITIONS

Figure 1:
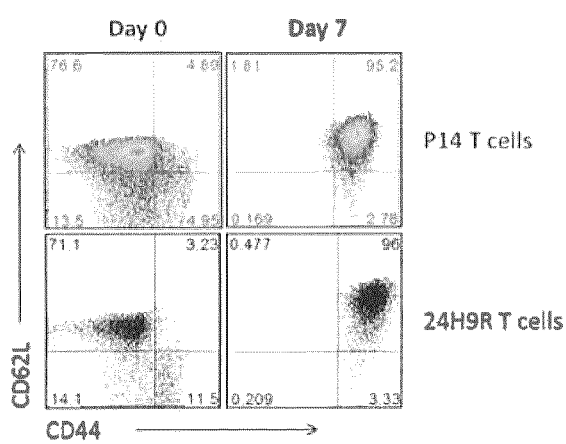
FIG. 1: Acquisition of central memory phenotype (CD44+ and CD62L+) of P14 or 24H9R CD8+ T cells cultured ex vivo with IL15, IL21, and rapamycin. The increasing expression of CD44 on CD8+, CD62L+ T cells from P14 mice (upper panels) or 24H9R mice (lower panels) at the indicated day post initiation are shown (A). Increasing cell numbers observed in the course of ex vivo culture are shown (B).
Figure 1:
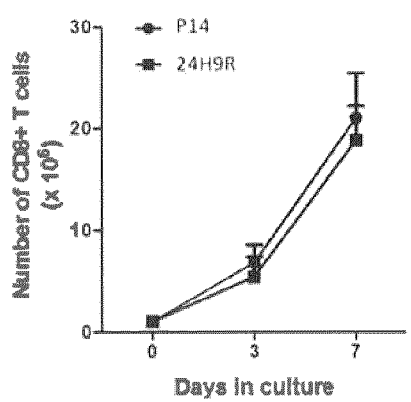

Unless otherwise indicated, the definitions and embodiments described in this and other sections are intended to be applied to all embodiments, and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

It is to be understood that "combination therapy" envisages the sequential administration to a subject of a population of tumor antigen-specific central memory T cells produced according to the ACT methods described herein and replicative oncolytic virus expressing the same tumor antigen or antigens. The memory T cell population produced according to the ACT methods described herein and the oncolytic virus expressing the same tumor antigen(s) are administered within time intervals that allow that the therapeutic agents show a cooperative e.g., synergistic, effect. In preferred embodiments, the memory T cell population and oncolytic virus are administered within about 1 hour to about 72 hours (e.g. within about 1, 2, 3, 6, 12, 24, 48, or 72 hours), within about 1 day to about 4 weeks (e.g. within about 1, 2 or 3 or 4 weeks), within about 1 week to about 3 weeks of each other or any range there between. In related embodiments, the memory T cell population and oncolytic virus are administered within 4, 5, 6, 7, 8, 9, 10, 11, 12, 13, 14, 15, 16, 17, 18, 19, 20, 21, 22, 23, 24, 25, 26, 27, 28, 29, 30 or 31 days of each other.

Terms of degree such as "substantially", "about" and "approximately" as used herein mean a reasonable amount of deviation of the modified term such that the result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a T cell" should be understood to present certain aspects with one substance or two or more additional substances.

In embodiments comprising an "additional" or "second" component, such as an additional or second cytokine, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

DETAILED DESCRIPTION

T Cells

In some embodiments, the combination therapy described herein utilizes adoptive transfer of tumor antigen-specific central memory T cells produced according to the methods herein described. Thus, it has been surprisingly discovered that culturing T cells (e.g. naïve T cells) in the presence of APCs, tumor antigen and a composition comprising or consisting essentially of IL21, IL15 and rapamycin results in a population of tumor antigen-specific T cells that is substantially enriched for T cells displaying a central memory phenotype compared to IL21, IL15 or rapamycin alone, which can be expanded ex vivo and introduced into a patient and followed with administration to the patient of an oncolytic virus expressing the same antigen to synergistically treat cancer without the need for costly cell sorting techniques and without the need to administer a lymphodepletion regimen to the patient prior to introducing the T cells and without the need for administering IL2 to the patient. In some embodiments, IL21 and IL15 are present at concentrations ranging from about 1 ng/ml to about 20 ng/ml, preferably about 10 ng/ml. In related embodiments, rapamycin is present at a concentration of from about 10 ng/ml to about 30 ng/ml, preferably about 20 ng/ml.

The APC may, for example, be an autologous dendritic cell which may be obtained by culturing adherent PBMCs with GM-CSF (e.g. about 800 U/ml) and IL-4 (e.g. about 500 U/ml) for about 5 days to differentiate them into dendritic cells. The resulting dendritic cells may be simulated by addition, on day 5, of TNFa (e.g. about 10 ng/ml), IL-1b (e.g. about 2 ng/ml), IL-6 (e.g. about 1000 U/ml), PGE-2 (e.g. about 1000 ng/ml), IL-4 (e.g. about 500 U/ml) and GM-CSF (e.g. about 800 U/ml) and cultured for more 2 days. On day 7, the dendritic cells may be pulsed with 40 µg/ml of peptide tumor antigen for about 2 hours and irradiated for use as tumor antigen peptide loaded APCs in accordance with the methods herein described.

In some embodiments, culturing naïve T cells in the presence of APCs, tumor antigen and IL21, IL15 and rapamycin results in a population of tumor antigen specific T cells, at least 50%, at least 60%, at least 70%, at least 80% or more of which display a central memory phenotype. In one embodiment, a central memory T cell obtained according to the ACT methods herein described displays a $CD44^+$ $CD62L^+$ $CD127^+$ phenotype.

T cells for use according to the ACT methods described herein can be obtained from blood, lymphoid tissue (e.g. spleen) or from a tumor (e.g. tumor infiltrating lymphocytes). In some embodiments, T cells for use according to the ACT methods described herein are produced from PBMCs that have a histcompatible phenotype to the subject with cancer to be treated. In related embodiments, the PBMCs are autologous to the subject with cancer to be treated.

In one preferred embodiment, a CD8+ human T cell population for use in adoptive cell transfer according to the present combination is obtained by culturing PBMCs obtained from a human cancer subject in the presence of IL21, IL15, and rapamycin, a tumor antigen expressed by the cancer and antigen presenting cells (e.g. from one to four weeks, preferably about three weeks), expanding the CD8+ human T cell population with anti-CD3 and anti-CD28 antibodies and IL2 and reintroducing the cells into the patient and subsequently (e.g. following a 24 hour interval) administering a replicative oncolytic virus (e.g. an oncolytic rhabdovirus) engineered to express a transgene encoding the same tumor antigen.

In a related embodiment, a CD8+ human T cell population for use in adoptive cell transfer according to the present combination is obtained by transducing a recombinant TCR or CAR specific for a tumor antigen expressed by a cancer in a human subject into PBMCs obtained from the subject, culturing the genetically modified cells in the presence of IL21, IL15, and rapamycin, antigen presenting cells and the tumor antigen (e.g. for about one to four weeks, preferably about three weeks), expanding the CD8+ human T cell population with anti-CD3 and anti-CD28 antibodies and IL2 and reintroducing the cells into the patient and subsequently (e.g. following a 24 hour interval) administering a replicative oncolytic virus (e.g. an oncolytic rhabdovirus) engineered to express a transgene encoding the same tumor antigen.

In another embodiment, a CD8+ human T cell population for use in adoptive cell transfer according to the present combination is obtained by culturing tumor infiltrating lymphocytes obtained from a human cancer subject in the presence of IL21, IL15, and rapamycin, a tumor antigen expressed by the cancer and antigen presenting cells (e.g. from one to four weeks, preferably about three weeks), expanding the CD8+ human T cell population with anti-CD3 and anti-CD28 antibodies and IL2 and reintroducing the cells into the patient and subsequently (e.g. following a 24 hour interval) administering a replicative oncolytic virus (e.g. an oncolytic rhabdovirus) engineered to express a transgene encoding the same tumor antigen.

In a related embodiment, a CD8+ human T cell population for use in adoptive cell transfer according to the present combination is obtained by transducing a recombinant TCR or CAR specific for a tumor antigen expressed by a cancer in a human subject into tumor infiltrating lymphocytes obtained from the subject, culturing the genetically modified cells in the presence of IL21, IL15, and rapamycin, antigen presenting cells and the tumor antigen (e.g. for about one to four weeks, preferably about three weeks), expanding the CD8+ human T cell population with anti-CD3 and anti-CD28 antibodies and IL2 and reintroducing the cells into the patient and subsequently (e.g. following a 24 hour interval) administering a replicative oncolytic virus (e.g. an oncolytic rhabdovirus) engineered to express a transgene encoding the same tumor antigen.

Oncolytic Viruses

Replication-competent oncolytic viruses expressing a tumor antigen of the combination include any naturally occurring (e.g. from a "field source") or modified replication-competent oncolytic virus. The oncolytic virus, in addition to expressing a tumor antigen, may for example, be modified to increase selectivity of the virus for cancer cell.

Replication-competent oncolytic viruses according to the invention include, but are not limited to, oncolytic viruses that are a member in the family of myoviridae, siphoviridae, podpviridae, teciviridae, corticoviridae, plasmaviridae, lipothrixviridae, fuselloviridae, poxyiridae, iridoviridae, phycodnaviridae, baculoviridae, herpesviridae, adnoviridae, papovaviridae, polydnaviridae, inoviridae, microviridae, geminiviridae, circoviridae, parvoviridae, hcpadnaviridae, retroviridae, cyctoviridae, reoviridae, birnaviridae, paramyxoviridae, rhabdoviridae, filoviridae, orthomyxoviridae, bunyaviridae, arenaviridae, Leviviridae, picornaviridae, sequiviridae, comoviridae, potyviridae, caliciviridae, astroviridae, nodaviridae, tetraviridae, tombusviridae, coronaviridae, glaviviridae, togaviridae, and barnaviridae.

Particular examples of replication-competent oncolytic viruses for use in the practice of the invention include adenovirus, retrovirus, reovirus, rhabdovirus, Newcastle Disease virus (NDV), polyoma virus, vaccinia virus (VacV), herpes simplex virus, picornavirus, coxsackie virus and parvovirus.

In some preferred embodiments, the replication competent oncolytic virus expressing a tumor antigen according to the combination is an oncolytic rhabdovirus.

The archetypal rhabdoviruses are rabies and vesicular stomatitis virus (VSV), the most studied of this virus family. Rhabdovirus is a family of bullet shaped viruses having non-segmented (−)sense RNA genomes. The family Rhabdovirus includes, but is not limited to: Arajas virus, Chandipura virus (AF128868/gi:4583436, AJ810083/gi:57833891, AY871800/gi:62861470, AY871799/gi:62861468, AY871798/gi:62861466, AY871797/gi:62861464, AY871796/gi:62861462, AY871795/gi:62861460, AY871794/gi:62861459, AY871793/gi:62861457, AY871792/gi:62861455, AY871791/gi:62861453), Cocal virus (AF045556/gi:2865658), Isfahan virus (AJ810084/gi:57834038), Maraba virus (SEQ ID ON:1-6 of U.S. Pat. No. 8,481,023, incorporated herein by reference; HQ660076.1), Carajas virus (SEQ ID NO:7-12 of U.S. Pat. No. 8,481,023, incorporated herein by reference, AY335185/gi:33578037), Piry virus (D26175/gi:442480, Z15093/gi:61405), Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus (DQ457103/gi:91984805), Perinet virus (AY854652/gi:71842381), Tupaia virus (NC_007020/gi:66508427), Bahia Grande virus (SEQ ID NO:13-18 of U.S. Pat. No. 8,481,023, incorporated herein by reference, KM205018.1), Muir Springs virus (KM204990.1), Reed Ranch virus, Hart Park virus, Flanders virus (AF523199/gi:25140635, AF523197/gi:25140634, AF523196/gi:25140633, AF523195/gi:25140632, AF523194/gi:25140631, AH012197/gi:25140630), Kamese virus, Mosqueiro virus, Mossuril virus, Barur virus, Fukuoka virus (AY854651/gi:71842379), Kern Canyon virus, Nkolbisson virus, Le Dantec virus (AY854650/gi:71842377), Keuraliba virus, Connecticut virus, New Minto virus, Sawgrass virus, Chaco virus, Sena Madureira virus, Timbo virus, Almpiwar virus (AY854645/gi:71842367), Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus (AY854643/gi:71842363), Joinjakaka virus, Kannamangalam virus, Kolongo virus (DQ457100/gi:91984799 nucleoprotein (N) mRNA, partial cds); Koolpinyah virus, Kotonkon virus (DQ457099/gi:91984797, AY854638/gi:71842354); Landjia virus, Manitoba virus, Marco virus, Nasoule virus, Navarro virus, Ngaingan virus (AY854649/gi:71842375), Oak-Vale virus (AY854670/gi:71842417), Obodhiang virus (DQ457098/gi|91984795), Oita virus (AB116386/gi:46020027), Ouango virus, Parry Creek virus (AY854647/gi:71842371), Rio Grande cichlid virus, Sandjimba virus (DQ457102/gi|91984803), Sigma virus (AH004209/gi:1680545, AH004208/gi:1680544, AH004206/gi:1680542), Sripur virus, Sweetwater Branch virus, Tibrogargan virus (AY854646/gi:71842369), Xiburema virus, Yata virus, Rhode Island, Adelaide River virus (U10363/gi:600151, AF234998/gi:10443747, AF234534/gi:9971785, AY854635/gi:71842348), Berrimah virus (AY854636/gi:71842350]), Kimberley virus (AY854637/gi:71842352), or Bovine ephemeral fever virus (NC_002526/gi:10086561). Any of these rhabdoviruses or variants thereof can be engineered to express a tumor antigen for use according to the combination.

In some preferred embodiments, the oncolytic rhabdovirus expressing a tumor antigen of the combination is a wild type or recombinant vesiculovirus, such as a wild type or recombinant VSV, Chandipura, Maraba, or Carajas, including variants thereof. In other embodiments, the oncolytic rhabdovirus is a wild type or recombinant non-vesiculovirus such as Muir Springs, Farmington, or Bahia grande virus, including variants thereof.

In a particularly preferred embodiment, the oncolytic virus expressing a tumor antigen of the combination is a wild type Maraba strain rhabdovirus or a variant thereof that has optionally been genetically modified e.g. to enhance tumor selectivity. The Maraba virus may be e.g. a Maraba virus containing a substitution at amino acid 242 of the G protein and/or at amino acid 123 of the M protein as described at col. 2, lines 24-42 of U.S. Pat. No. 9,045,729, the entire contents of which are incorporated herein by reference. In a particularly preferred embodiment, the Maraba virus is Maraba MG1 as described in Brun et al., Mol. Ther., 18(8):1440-1449 (2010). Maraba MG1 is a genetically modified Maraba strain rhabdovirus containing a G protein mutation (Q242R) and an M protein mutation (L123W) that renders the virus hypervirulent in cancer cells yet attenuated in normal cells.

In another preferred embodiment, the oncolytic rhabdovirus expressing a tumor antigen of the combination is a VSV strain or a variant thereof that has optionally been genetically modified e.g. to enhance tumor selectivity. In a particularly preferred embodiment, the VSV comprises a deletion of methionine at position 51 of the M protein as described in Stojdl et al., Cancer Cell., 4(4):263-75 (2003), the contents of which are incorporated herein by reference.

A replicative oncolytic rhabdovirus expressing a tumor antigen of the combination may be systemically administered, preferably by intravascular (intravenous and/or intraarterial) administration, which includes injection, perfusion and the like, to a subject after ACT therapy according to the methods described herein as one or more doses of 10, 100, $10^3$, $10^4$, $10^5$, $10^6$, $10^7$, $10^8$, $10^9$, $10^{10}$, $10^{11}$, $10^{12}$, $10^{13}$, $10^{14}$, or more viral particles (vp) or plaque forming units (pfu). In preferred embodiments, the oncolytic rhabdovirus expressing a tumor antigen is intravascularly administered to a subject after ACT therapy according to the methods described herein as one or more dosages of $10^5$-$10^{14}$pfu, $10^6$-$10^{12}$ pfu, $10^8$-$10^{14}$ pfu or $10^8$-$10^{12}$ pfu.

In some preferred embodiments, the replication competent oncolytic virus expressing a tumor antigen of the combination is an oncolytic vaccinia virus, In preferred embodiments, the replicative oncolytic vaccinia virus expressing a tumor antigen of the combination is a Copenhagen, Western Reserve, Lister or Wyeth strain. The genome of the Western Reserve vaccinia strain has been sequenced (Accession number AY243312).

The replicative oncolytic vaccinia virus expressing a tumor antigen may be engineered to lack one or more functional genes in order to increase the cancer selectivity of the virus. In some preferred embodiments, the oncolytic vaccinia virus is engineered to lack thymidine kinase (TK) activity. In another aspect, the oncolytic vaccinia virus may be engineered to lack vaccinia virus growth factor (VGF). In another aspect, the oncolytic vaccinia virus may be engineered to lack both VFG and TK activity. In other aspects, the oncolytic vaccinia virus may be engineered to lack one or more genes involved in evading host interferon (IFN) response such as E3L, K3L, B18R, or B8R. In some preferred embodiments, the replicative oncolytic vaccinia virus is a Western Reserve, Copenhagen, Lister or Wyeth strain and lacks a functional TK gene. In other embodiments, the oncolytic vaccinia virus is a Western Reserve, Copenhagen, Lister or Wyeth strain lacking a functional B18R and/or B8R gene.

A replicative oncolytic vaccinia virus expressing a tumor antigen of the combination may be locally or systemically administered to a subject, e.g. via intratumoral, intraperitoneal, intravenous, intra-arterial, intramuscular, intradermal, intracranial, subcutaneous, or intranasal administration following ACT therapy according to the methods described herein as one or more dosages of $1\times10^5$ plaque forming units (pfu), $5\times10^5$ pfu, at least $1\times10^6$ pfu, $5\times10^6$ or about $5\times10^6$ pfu, $1\times10^7$, at least $1\times10^7$ pfu, $1\times10^8$ or about $1\times10^8$ pfu, at least $1\times10^8$ pfu, about or at least $5\times10^8$ pfu, $1\times10^9$ or at least $1\times10^9$ pfu, $5\times10^9$ or at least $5\times10^9$ pfu, $1\times10^{10}$ pfu or at least $1\times10^{10}$ pfu, $5\times10^{10}$ or at least $5\times10^{10}$ pfu, $1\times10^{11}$ or at least $1\times10^{11}$, $1\times10^{12}$ or at least $1\times10^{12}$, $1\times10^{13}$ or at least $1\times10^{13}$ pfu. For example, the virus may be administered at a dosage of between about $10^7$-$10^{13}$ pfu, between about $10^8$-$10^{13}$ pfu, between about $10^9$-$10^{12}$ pfu, between about $10^8$-$10^{12}$, or between $10^9$ and $10^{10}$ pfu.

It is contemplated that a single dose of oncolytic virus expressing a tumor antigen refers to the amount administered to a subject or a tumor over a 0.1, 0.5, 1, 2, 5, 10, 15, 20, or 24 hour period, including all values there between. The dose may be spread over time or by separate injection. Typically, multiple doses are administered to the same general target region, such as in the proximity of a tumor or in the case of intravenous administration a particular entry point in the blood stream or lymphatic system of a subject. In certain aspects, the viral dose is delivered by injection apparatus comprising a needle providing multiple ports in a single needle or multiple prongs coupled to a syringe, or a combination thereof. A single dose of the oncolytic virus may be administered or multiple doses may be administered over a treatment period that may comprise 1, 2, 3, 4, 5, 6, 7, 8, 9, 10, 11, 12 or more weeks. For example, the oncolytic virus may be administered every other day, weekly, every other week, every third week for a period of 1, 2, 3, 4, 5, 6 or more months.

As will be appreciated by one of skill in the art, the oncolytic virus expressing a tumor antigen is normally administered as part of a pharmaceutical composition along with a pharmaceutically acceptable carrier, such as saline or other suitable buffer. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions Tumor Antigens Oncolytic viruses of the combination express the same antigen targeted by T cells produced by the ACT methods described herein. Suitable antigens that may be expressed by the oncolytic virus include without limitation, oncofetal antigens such as alphafetoprotein (ALF) and carcinoembryonic antigen (CEA), surface glycoproteins such as CA 125, oncogenes such as Her2, melanoma-associated antigens such as dopachrome tautomerase (DCT), GP100 and MART-1, cancer-testes antigens such as the MAGE proteins and NY-ESO-1, viral oncogenes such as HPV E6 and E7, and proteins ectopically expressed in tumors that are usually restricted to embryonic or extraembryonic tissues such as PLAC1 or a variant of a tumor-associated antigen. A "variant" of a tumor associated antigen refers to a protein that (a) includes at least one tumor associated antigenic epitope from the tumor associated antigenic protein and (b) is at least 70%, preferably at least 80%, more preferably at least 90% or at least 95% identical to the tumor associated antigenic protein. A database summarizing well accepted antigenic epitopes is provided by Van der Bruggen P, Stroobant V, Vigneron N, Van den Eynde B in "Database of T cell-defined human tumor antigens: the 2013 update." Cancer Immun 2013 13:15, available online at www.cancerimmunity.org/peptide.

In some embodiments, the oncolytic virus expresses MAGEA3, Human Papilloma Virus E6/E7 fusion protein, human Six-Transmembrane Epithelial Antigen of the Prostate protein, or Cancer Testis Antigen 1.

In other embodiments, the present invention provides a method for identifying a tumor antigen comprising co-culturing PBMCs with tumor material isolated from a subject in the presence of a composition comprising or consisting essentially of IL21, IL15, and rapamycin and antigen presenting cells (e.g. dendritic cells); isolating a T cell population from the culture; cloning individual T cells from the T cell population; and characterizing T cell clones for antigen-specificity. In some embodiments, the tumor material comprises total RNA, lysed tumor cells or apoptotic bodies. The ACT methods herein described can be used to generate a population of central memory T cells specific for an antigen identified by the method and combined with an oncolytic virus engineered to express the same antigen to provide a synergistic cancer treatment.

Cancers

Cancers to be treated according to the combination described herein include, without limitation, leukemia, acute lymphocytic leukemia, acute myelocytic leukemia, myeloblasts promyelocyte, myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (including small cell lung cancer, squamous non-small cell lung cancer and non-squamous non-small cell lung cancer)), melanoma (including metastatic melanoma), neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. In some preferred embodiments, the cancer to be treated is selected from non-small cell lung cancer (NSCLC), breast cancer (e.g. hormone refractory metastatic breast cancer), head and neck cancer (e.g. head and neck squamous cell cancer), metastatic colorectal cancer, hormone sensitive or hormone refractory prostate cancer, colorectal cancer, ovarian cancer, hepatocellular cancer, renal cell cancer, soft tissue sarcoma and small cell lung cancer.

In one aspect, the subject to be treated with the combination is a human with a cancer that is refractory to treatment with one or more chemotherapeutic agents and/or refractory to treatment with one or more antibodies.

EXAMPLES

The following example illustrates the scope of the invention. Specific elements of the example are for descriptive purposes only and are not intended to limit the scope of the invention. Those skilled in the art could develop equivalent methods and utilize comparable materials that are within the scope of the invention.

Experimental Methods and Procedures

Cell Lines

All cells were maintained at 37° C. in a humidified atmosphere with 5% CO2. B16F10 and B16gp33 cells (which are B16F10 cells engineered to express a mini-gene corresponding to the LCMV gp33 epitope) were maintained in MEM/F11 containing 10% FBS, 2 mM L-glutamine, 5 ml sodium pyruvate, 5 ml nonessential amino acids, 5 ml vitamin solution, 55 µM 2-mercaptoethanol, 100 U/mL penicillin and 100 ng/mL streptomycin. Expression of the gp33 mini-gene was maintained with 800 µg/ml G418. All cell culture reagents from Invitrogen (Invitrogen, Grand Island, N.Y.). CMS5 cells were maintained in DMEM containing 10% FBS, 2 mM L-glutamine, 100 U/mL penicillin and 100 ng/mL streptomycin.

Animals

C57BL/6 and BALB/c mice were purchased from Charles River Laboratory (Wilmington, Mass.) and housed in a specific pathogen-free facility. DUC18 mice, transgenic mice engineered to express the T cell receptor specific for the syngeneic CMS5 fibrosarcoma rejection antigen mutated Erk9M(136-144), where a kind gift from Lyse Norian (University of Iowa, Iowa). 24H9R mice, a transgenic mouse strain that bears a TCR transgene that recognizes an $H-2K^b$—restricted epitope of DCT/TRP-$2_{180-188}$, where the kind gift of Dr. Arthur Hurwitz (NIH, Frederick, Md.). P14 mice, a transgenic mouse strain that carries the TCR for the gp33 peptide (B6.Cg-Tcrd$^{tm1Mom}$ Tg(TcrLCMV)327Sdz), were purchased from Taconic Breeding Laboratories (Germantown, N.Y.). B6.Cg-Tg(Ins2-GP)34-20Olds transgenic mice (referred to as RIPgp mice) were the kind gift from Pamela Ohashi (UHN Research, Toronto, Canada) and were bred in the Central Animal Facility at McMaster University. NRG mice (Cg-Rag1$^{tm1Mom}$ Il2rg$^{tm1Wjl}$/SzJ) were purchased from The Jackson Laboratory (Farmington, Conn.). All animal studies complied with Canadian Council on Animal Care guidelines and approved by McMaster University's Animal Research Ethics Board.

Skin Tumor Animal Models

Six to eight-week-old BALB/c, C57BL/6 or RIPgp mice were challenged intradermally with $2\times10^5$ B16-gp33 or B16F10 cells or $10^6$ CMS5 cells, ACT and subsequent OV vaccinations were administered 5 to 7 days post tumor implantation (when tumors reached ~5 mm diameter). Tumor growth was monitored daily and measured with calipers every other day. Tumor volume was calculated as width×length×depth. Tumor endpoint was defined as >10 mm in at least two dimensions or >20 mm in one dimension. Where required, blood glucose levels were monitored using a Contour next glucometer (Ascensia Diabetes). Animals that showed >14 mmol/L blood glucose were considered diabetic.

Viruses

VSV-gp33 [22] and VacV-gp33 [23] vectors are recombinant vesicular stomatitis and vaccinia viruses respectively, which express the dominant CD8$^+$ and CD4$^+$ T-cell epitopes of the lymphocytic choriomeningitis virus glycoprotein (LCMV-gp$_{33-41}$ and LCMV-gp$_{61-80}$, respectively). MRB-GP is a pseudotyped recombinant Maraba virus which has its native glycoprotein genetically replaced with the glycoprotein of LCMV. VSV-hDCT and MRB-hDCT are recombinant vesicular stomatitis and Maraba viruses respectively, which express the full-length human dopachrome tautomerase (DCT) [24]. VacV-hDCT is a recombinant, thymidine kinase and vaccinia growth factor double-deleted vaccinia virus engineered to express hDCT. Ad-hDCT is a replication deficient adenovirus (E1/E3 deletion) based on the human serotype 5 encoding full length human melanoma antigen DCT [24]. VSV-Erk9M and MRB-Erk9M are recombinant vesicular stomatitis and Maraba viruses respectively, which express the dominant CD8+ T-cell epitope for the mutant form of ERK expressed in the CMS5 cell line. VSV-gp33 and VSV-hDCT were modified to abrogate their ability to inhibit Type I IFN responses via deletion of the methionine residue at position 51 of the matrix protein as described previously [25]. MRB-hDCT and MRB-Erk9M were also modified to abrogate their ability to inhibit Type I IFN responses through mutation of a residue in the matrix and a residue in the glycoprotein as previously described [26].

Peptides

The H-2Db-restricted peptide of LCMV-GP (gp$_{33-41}$; KAVYNFATM (SEQ ID NO. 1)), the H-2Kb-restricted peptide of DCT (DCT$_{180-188}$ SVYDFFVWL (SEQ ID NO. 2)), and the H-2Kd-restricted peptide of mutant ERK (Erk9M$_{136-144}$; QYIHSANVL (SEQ ID NO. 3)) were purchased from Biomer Technology (Pleasanton, Calif.). Peptides were dissolved in distilled water and stored at −20° C.

Ex Vivo Tcm Culture and ACT+Vaccination Protocol

Splenocytes were isolated from TCR transgenic mice by conventional methods. Splenocytes (containing a large number of APCs) were seeded at a density 3 million/mL in RPMI media supplemented with 10% fetal bovine serum (FBS), 2 mM L-glutainine, 55 μM 2-mercaptoethanol, 100 U/mL penicillin, 100 ng/mL streptomycin, 10 ng/mL IL21, 10 ng/mL IL15, 20 ng/mL Rapamycin and 0.1 μg/mL cognate antigenic peptide. Four days after initial seeding, cultures were expanded 5 fold in volume using the initial media and supplements without peptide. Cells were harvested 3 days later, washed and suspended in PBS for injection. Mice were injected intravenously (IV) with $10^6$ Tcm cells in 200 μL of PBS and 24 hours later, $2\times10^8$ pfu of VSV-gp33, VSV-DCT and MRB-DCT, $1\times10^8$ pfu of VacV-gp33 and VacV-DCT, $5\times10^8$ pfu VSV-erk9m and MRB-erk9m was injected IV in 200 μL of PBS (unless otherwise stated). Lymphodepletion treatment was performed where indicated via IP injection of 20 mg/kg cyclophosphamide (CPX) 3 days before infusion of Tcm cells.

Flow Staining for Tcm Surface Markers

Ex vivo cultured cells were harvested, pelleted and treated with Fc block. Cells were then stained for surface expression of CD8, CD44, CD62L, and CD127. Data were acquired using an LSRFortessa with FACSDiva software (BD Biosciences, Mississauga, ON, Canada) and analyzed with FlowJo software (Tree Star, Ashland, Oreg.).

Detection of Antigen-Specific T-Cell Responses

Periphral blood mononuclear cells were obtained from periorbital sinus blood samples. Red blood cells were lysed with ACK lysis buffer. Mononuclear cells were stimulated with gp33 peptide (1 μg/mL) at 37° C. for 5 hours and brefeldin A (Golgi Plug, 1 μg/mL; BD Biosciences) was added during the last 4 hours of incubation. Cells were treated with Fc block and stained for surface expression of CD8. Cells were subsequently fixed, permeabilized (Cytofix/Cytoperm, BD Biosciences) and stained for intracellular interferon-γ. Data were acquired using an LSR-Fortessa with FACSDiva software (BD Biosciences) and analyzed with FlowJo software (Tree Star, Ashland, Oreg.).

Histopathology and Immunohistochemical Staining

Tissues were fixed in 10% formalin for 24 hours before dehydration in 70% ethanol. Fixed tissues were embedded in paraffin and sectioned at 5 μm. Sections were either stained with haematoxylin and eosin or probed for insulin expression by immunohistochemistry (IHC). For IHC, sections were treated with 3% hydrogen peroxide for 15 min at room temperature and blocked with 5% BSA and 2% goat serum in PBS containing 0.2% Triton X-100 for 45 min and subsequently treated with avidin/biotin blocking kit (Vector labs). Slides were incubated overnight at 4° C. with rabbit anti-mouse insulin antibody (abcam; ab181547) followed by incubation with biotinylated anti-rabbit antibody (Vector labs). Slides were developed using sequential treatment with Vectastain ABC kit (Vector labs) and ImmPACT AMEC Red peroxidase substrate kit (Vector labs) before counterstaining with Harris' hematoxylin and mounting using Permount (Fisher).

Example 1

Ex Vivo Culture of TAA-Specific CD8 T Cells Induces a Central Memory Phenotype

Ex vivo based T cell cultures commonly utilize cytokines that signal through the common gamma chain (IL2Rγ or CD132). Common gamma chain family cytokines include, but are not limited to IL2, IL15, and IL21 [27]. CD132 is mainly expressed on lymphocytes and signaling through this receptor drives proliferation and maturation of CD8+ T cells and other lymphocyte subtypes [27]. IL2 is known to induce rapid proliferation and effector differentiation of CD8 T cells [28-30] whereas IL15 and IL21 are known to drive slower, homeostatic proliferation and bias CD8+ T cells towards a central memory differentiation status [30-32]. Therefore, we utilized IL15, and IL21 supplementation in our ex vivo culture system. In addition, we also employed rapamycin, a commonly used mTOR inhibitor. Regulation of the mTOR pathway has been shown to support survival of T cells and induce memory T cell differentiation in viral vaccine systems [33,34]. Short course in vivo treatment with rapamycin can augment memory T cell differentiation and enhance anti-tumor efficacy of vaccine-induced T cells [35]. Consequently, combination of IL15, IL21, and rapamycin in our T cell culture protocol allows for expansion of T cells and acquisition of central memory phenotype and functionality.

In order to establish a Tcm culture, splenocytes were extracted from P14 or 24H9R mice and cultured for 7 days in the presence of 0.1 μg/mL of gp33 or DCT peptide, 20 ng/mL of rapamycin and 10 ng/mL each of IL15 and IL21. At 3 days post initiation, the culture volume was expanded fivefold with standard T cell media (RPMI media with L-glutamine, antibiotics and betamercaptoethanol) supplemented with 20 ng/mL of rapamycin and 10 ng/mL each of IL15 and IL21 in the absence of peptide. Prior to culture, P14 CD8 T cells (FIG. 1A, day 0) were CD44 negative but positive for CD62L, a classic naïve T cell phenotype. Upon harvest after 7 days of ex vivo culture (FIG. 1A, day 7) cells still displayed a central memory phenotype with high level expression of both CD44 and CD62L. In addition to acquiring the Tcm phenotype, cultured cells showed robust proliferation with both P14 and 24H9R based cultures expanding approximately 20-fold in 7 days based upon total cell yield calculated from cell counts (FIG. 1B). Tumor antigen stimulation in combination with TL-15 drive proliferation of the T cells; IL-21 and rapamycin induce a central memory differentiation and rein in the proliferation of T cells so that they do not become effector T cells.

Example 2

The Specific Combination of IL21, IL15, and Rapamycin is Required for Guided Differentiation of Antigen-Specific Central Memory CD8+ T Cells with Optimal Anti-Tumor Effect in the Combination Therapy.

The specific combination of rapamycin, IL15, and IL21 is required for ex vivo culture, expansion and differentiation of antigen-specific central memory CD8+ T cells with optimal anti-tumor effect in the combination therapy described herein. Each, and all, of these components are required to generate such Tcm cells and cells produced in the absence of one or more of these components have sub-optimal T cell expansion and/or reduced anti-tumor effect after in vivo infusion and OV vaccination.

Figure 2:
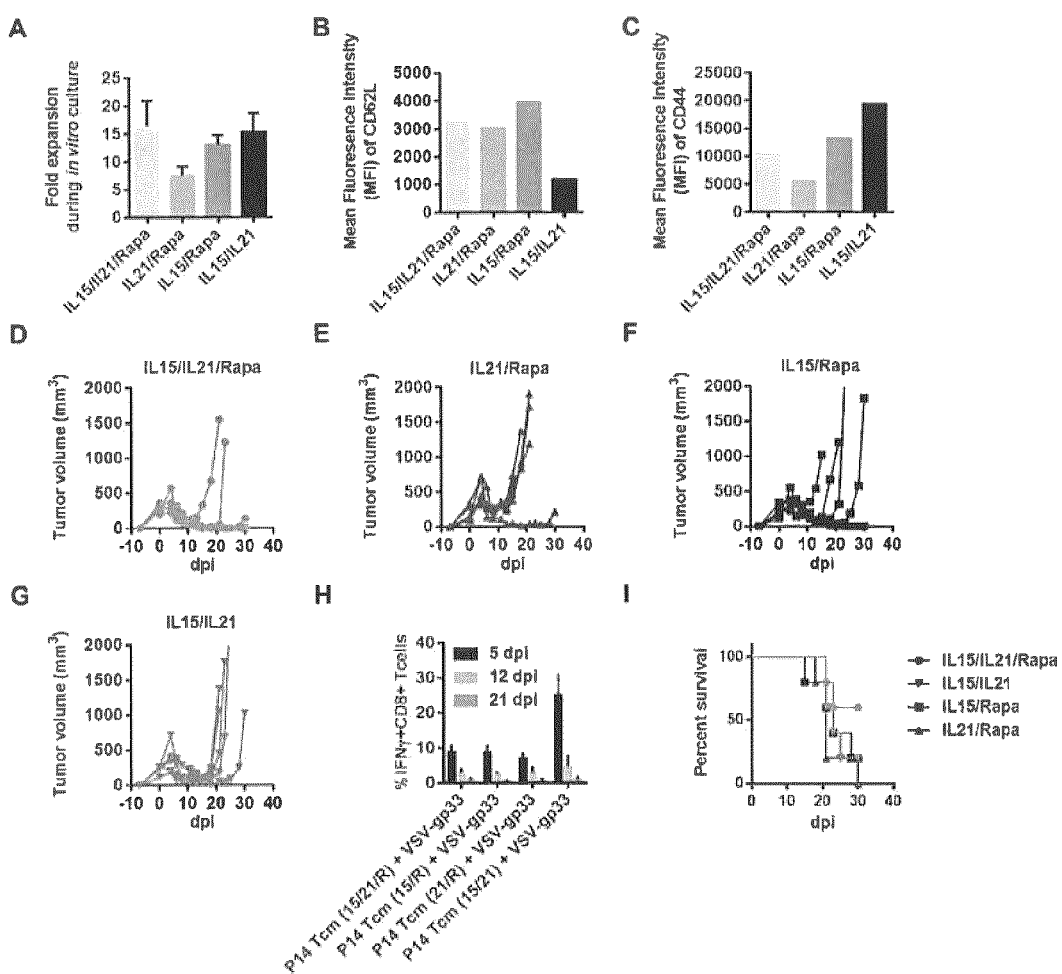
FIG. 2: Combinatorial use of IL15, IL21 and Rapamycin is required during ex vivo culture to generate Tcm cells with optimal anti-tumor effect in the combination therapy. Fold expansion (A) as well as CD62L (B) and CD44 (C) expression level of P14 CD8 T cells after 7 days of ex vivo culture with the indicated combinations of IL15, IL21 and rapamycin are shown. Tumor volume was measured using calipers and expressed as $mm^3$ at each indicated day post infection (dpi) with 0 dpi representing the day of oncolytic virus injection. Tumor volume results for mice treated with VSV-gp33 after infusion of P14 cells cultured with the indicated combinations of IL15, IL21 and rapamycin are shown (D-G). Responses at 5, 12 and 21 days post infection are expressed as the % of CD8+ T cells in the peripheral circulation that produce interferon γ (IFNγ) upon stimulation with the $gp33_{33-41}$ peptide (H). The percent of mice in panels D-G maintaining a tumor size below 1000 $mm^3$, the cut-off for tumor endpoint, is shown (I).

IL15 is required in the culture protocol to drive CD8+ T cell expansion and central memory differentiation. Cells cultured in the absence of IL15 showed impaired proliferation and a reduced cell yield from the ex vivo culture (IL21/Rapa in FIG. 2A) compared to cells grown in the full combination (IL15/IL21/Rapa in FIG. 2A). In addition, cells cultured this way displayed an altered phenotype skewed towards a naïve (reduced CD44 level in FIG. 2C) rather than central memory phenotype—as exemplified by cells grown the full combination in FIGS. 2B and C. Upon infusion and VSV-gp33 stimulation, cells grown in the absence of IL15 yielded a slightly reduced magnitude of antigen-specific CD8 T cell response (FIG. 2H) and were unable to completely regress the tumor or extend survival (FIGS. 2E and I).

IL21 plays an integral role in programming the cultured cells into good quality central memory phenotype with optimal antigen-specific cytolytic function. Cells cultured in the absence of IL21 (IL15/Rapa) had normal expression levels of CD62L (FIG. 2B) and CD44 (FIG. 2C) with comparable ex vivo proliferation to cells cultured with the full combination. After infusion and stimulation with VSV-gp33 the cells grown in the absence of IL21 yielded an in vivo response with comparable magnitude to that of cells cultured with the full combination. Regardless, tumor regression (FIG. 2F) and survival (FIG. 2I) of mice treated with cells grown in the absence of IL21 was inferior compared to cells grown with the full combination.

Rapamycin exerts an inhibitory function on the proliferation of antigen-specific CD8+ T cells, which doesn't interfere with the acquisition of a Tcm phenotype. Instead the role of rapamycin in the culture regimen described here is to enhance cell quality in terms of cytolytic function and anti-tumor effect after OV stimulation. Cells generated in the absence of rapamycin show equivalent proliferation ex vivo (IL15/Il21 group in FIG. 2A) but show altered expression of central memory T cell marker proteins CD62L and CD44 (FIGS. 2A and B, respectively) compared to cells grown in the full combination. Decreased CD62L expression in these cells suggests that they have not acquired a true central memory differentiation status. Indeed, cells grown in the absence of rapamycin showed enhanced proliferation in vivo five days after OV stimulation (FIG. 2H). This was short lived and by 12 and 21 days post infection the level of antigen-specific CD8 T cells dropped to levels comparable to cells grown in the full combination. Taken together these results indicate that cells grown in the absence of rapamycin adopt an effector memory phenotype (30) and are more susceptible to death signals delivered in vivo after VSV-gp33 stimulation. In the end, these cells have impaired anti-tumor efficacy, showing a lack of complete tumor regression (FIG. 2G) leading to reduced survival (FIG. 2I).

Example 3

Figure 3:
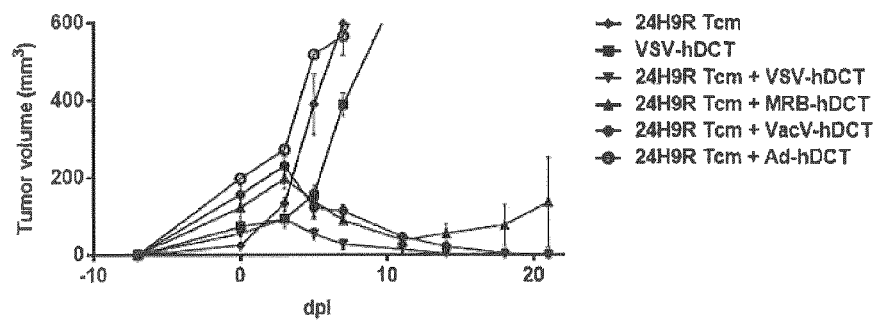
FIG. 3: 24H9R Tcm ACT+OV-hDCT combination therapy induces robust antigen-specific T cell response and regression of B16F10 tumors. Tumor volume was measured using calipers and expressed as $mm^3$ at each indicated day post infection (dpi) with 0 dpi representing the day of oncolytic virus injection (A). Responses at 5, 12 and 21 days post infection are expressed as the % of CD8+ T cells in the peripheral circulation that produce interferon γ (IFNγ) upon stimulation with the $DCT_{180-188}$ peptide (B).
Figure 3:
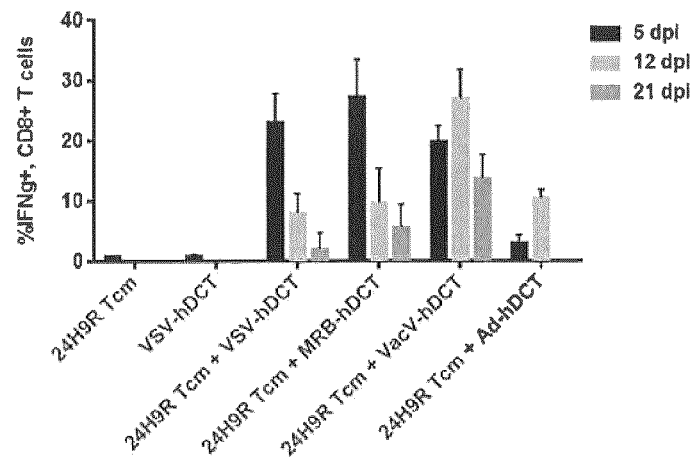
Figure 4:
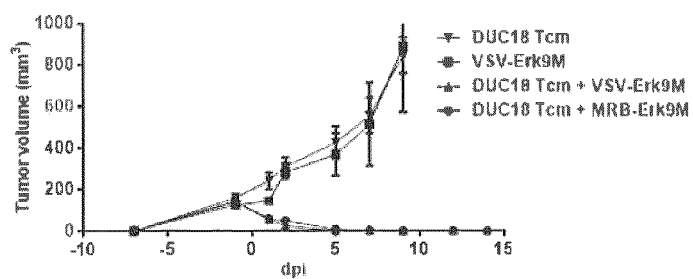
FIG. 4: DUC18 Tcm ACT+OV-Erk9M combination therapy induces robust antigen-specific T cell response and regression of CMS5 tumors. Tumor volume was measured using calipers and expressed as $mm^3$ at each indicated day post infection (dpi) with 0 dpi representing the day of oncolytic virus injection (A). Responses at 5, 12 and 21 days post infection are expressed as the % of CD8+ T cells in the peripheral circulation that produce interferon γ (IFNγ) upon stimulation with the $Erk9M_{136-144}$ peptide (B). Tumor volume of mice previously cured using Tcm+OV-Erk9M therapy and re-challenged with CMS5 cells were measured using calipers and expressed as $mm^3$ at each day post challenge as indicated (C).
Figure 4:
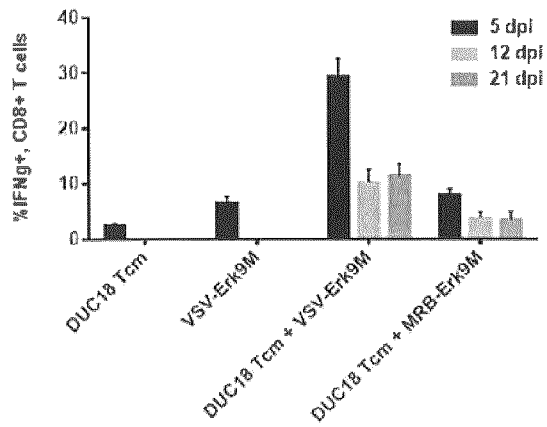
Figure 4:
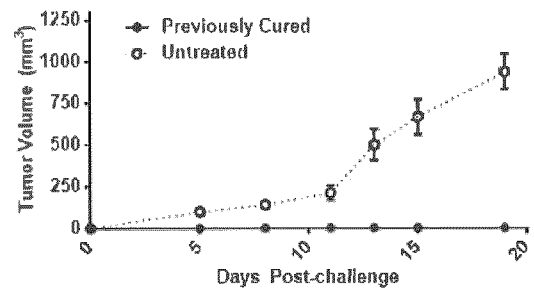
Figure 5:
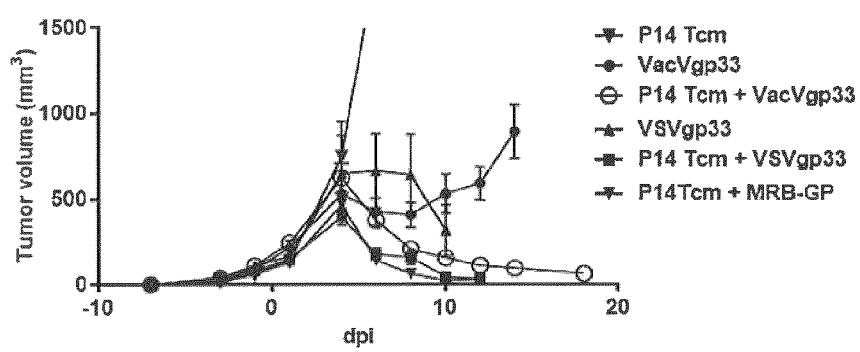
FIG. 5: P14 Tcm ACT+OV-gp33 combination therapy induces robust antigen-specific T cell response and regression of B16-gp33 tumors. Tumor volume was measured using calipers and expressed as $mm^3$ at each indicated day post infection (dpi) with 0 dpi representing the day of oncolytic virus injection. Results for VacV-gp33, VSV-gp33 and MRB-gp33 injection are shown (A). Responses at 5 and 12 days post infection are expressed as the % of CD8+ T cells in the peripheral circulation that produce interferon γ (IFNγ) upon stimulation with the gp33$_{33-41}$ peptide (B).
Figure 5:
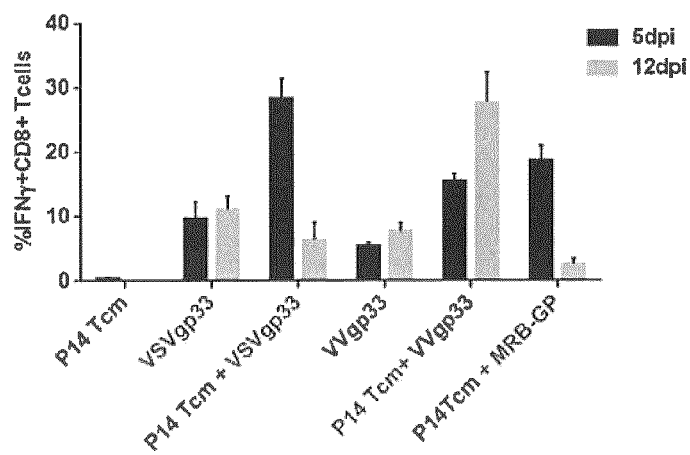

Transfer of Ex Vivo Cultured Memory T Cells Requires OV Vaccine Boost to Acquire Anti-Tumor Activity Central memory CD8 T cells reside in the lymph nodes and remain inactive until stimulated via presentation with their cognate peptide. Upon antigen-specific stimulation, Tcm cells rapidly divide and differentiate into effector cells to generate a robust systemic cytolytic response. The antigen-specific cytolytic function of ex vivo culture generated Tcm cells was tested via adoptive transfer into mice bearing tumors expressing the antigen targeted by the transferred cells followed by activation with an oncolytic virus vaccine expressing the same antigen. We tested three TCR transgenic mouse strains (24H9R, DUC18, and P14 mice) which target antigens expressed on commonly used tumor cell line models representing a true self antigen, a neoantigen and a viral antigen (DCT in B16F10 cells, Erk9M in DUC18 cells, and B16-gp33 cells, respectively). Cultured Tcm cells were adoptively transferred into mice bearing a tumor expressing the antigenic target of the T cells. Transfer of Tcm cells alone was unable to induce a significant systemic antigen-specific response and did not show any anti-tumor effect (Tcm group in FIGS. 3, 4, and 5). This is an expected characteristic of Tcm cells as they are sequestered to the lymphatic organs where they encounter minimal levels of peptide. Since antigen presentation is a prerequisite for activation of Tcm cells and development of an effector response we combined our Tcm ACT with oncolytic virus vaccine vectors expressing the cognate peptide. We chose to use vesicular stomatitis virus, Maraba virus and vaccinia virus vectors since they are oncolytic viruses and have been used as vaccine vectors in the past. These viruses have potent oncolytic activity, meaning that they preferentially infect and lyse cancer cells, so they can synergistically enhance CD8 mediated tumor destruction. Inclusion of a transgene cassette into these viral vectors that correlates with the peptide specificity of the transferred T cells generates an oncolytic vaccine and allows for delivery of the peptide to the lymph node and activation of the previously administered Tcm ACT cells. Tcm ACT induced rapid and complete tumor regression when combined with VSV, MRB (FIGS. 3A, 4A, and 5A), and VacV vaccination (FIGS. 3A and 5A). The CD8 T cell response induced with the combination therapies was pronounced with an average peak response of about 10 to 30% IFNγ+ CD8 T cells at five days post infection for VSV and Maraba (FIGS. 3B, 4B, and 5B) and 12 days post infection for VacV (FIGS. 3B and 5B). Combination of the oncolytic vaccines with ACT is required as both VSV-gp33 and VacV-gp33 vaccination alone were unable to induce complete tumor regression in the gp33 model (FIG. 5A) despite inducing a significant response against the gp33 peptide (FIG. 5B). A delay in tumor outgrowth was observed, but ultimately the tumor overcame the immune attack and growth inhibition levied by the oncolytic vaccine. This could be because the tumor growth outpaces the developing anti-tumor immune response. Alternatively, the immunosuppressive influence of the tumor could be rendering the gp33-specific cells induced by the oncolytic vaccine alone dysfunctional. These data indicate combining Tcm ACT and oncolytic vaccine therapy induces complete immune mediated tumor regression where either treatment alone cannot.

Use of a non-oncolytic adenovirus vaccine vector (Ad-hDCT in FIG. 3) in combination with Tcm ACT failed to control tumor growth (FIG. 3A) despite inducing significant expansion and activation of transferred Tcm cells with a peak response of about 10% IFNγ+ CD8 T cells at 12 days post infection (FIG. 3B). This indicates that oncolytic virus vaccine vectors (such as VSV, MRB, and VacV) are ideally suited for activation of ACT Tcm and are required for complete and tumor response in this combination therapy.

The anti-tumor properties of the combination therapy were not only able to completely regress tumors but also persisted at least 60 days and suppressed subsequent engraftment and growth of antigen matched tumor cells. BALB/c mice that were treated and cured of CMS5 tumors by combination treatment with DUC18Tcm and VSV-Erk9M 60 days previously were re-challenged with an intradermal injection of CMS5 tumor cells. Rapid tumor growth was observed in naïve control mice but was absent in mice previously cured (FIG. 4C), showing that the response induced by the combination therapy persists and suppresses outgrowth of any new tumor cells expressing the targeted antigen.

Example 4

Injection Route Dependence of OV Mediated P14 Tcm Activation

Figure 6:
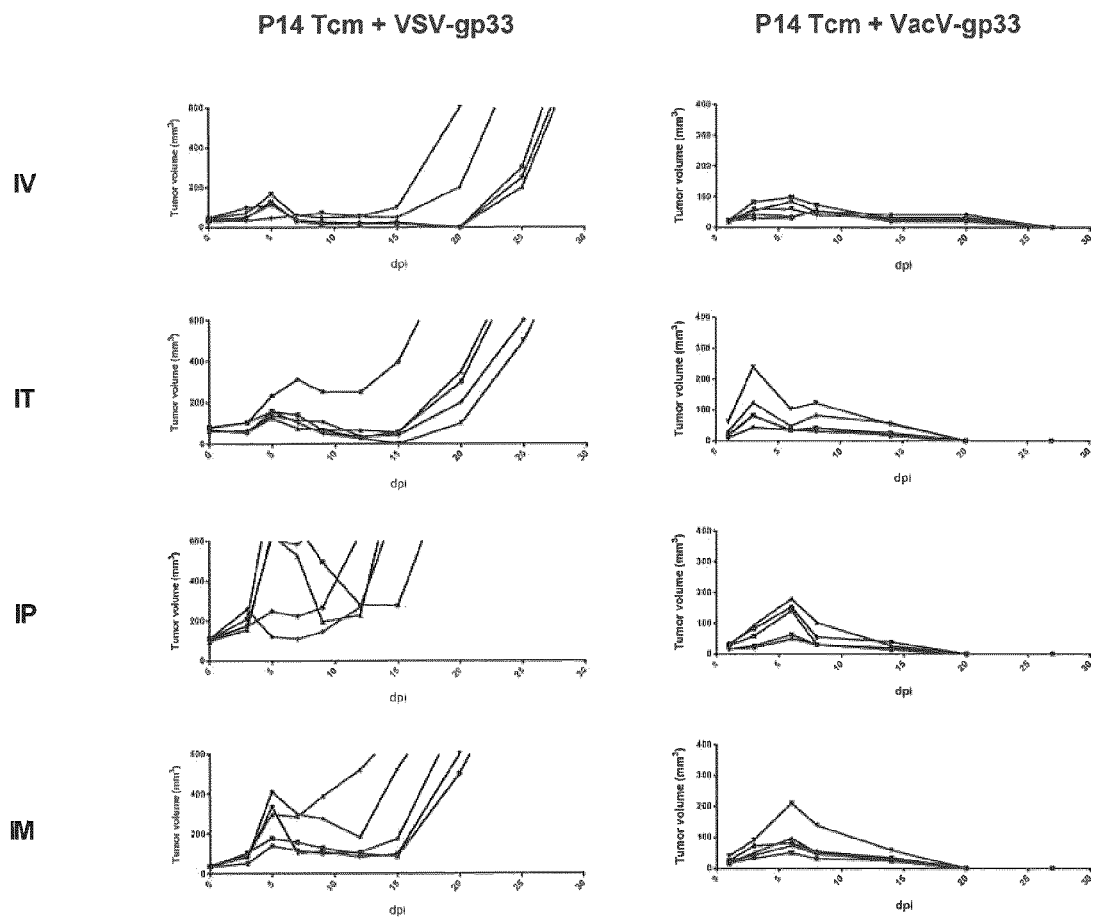
FIG. 6: Tumor regression efficacy of P14 Tcm ACT+OV boost when virus is administered by IV, IT, IP, and IM injection route. Tumor volume was measured using calipers and expressed as mm$^3$ at each indicated day post infection (dpi) with 0 dpi representing the day of oncolytic virus injection.
Figure 7:
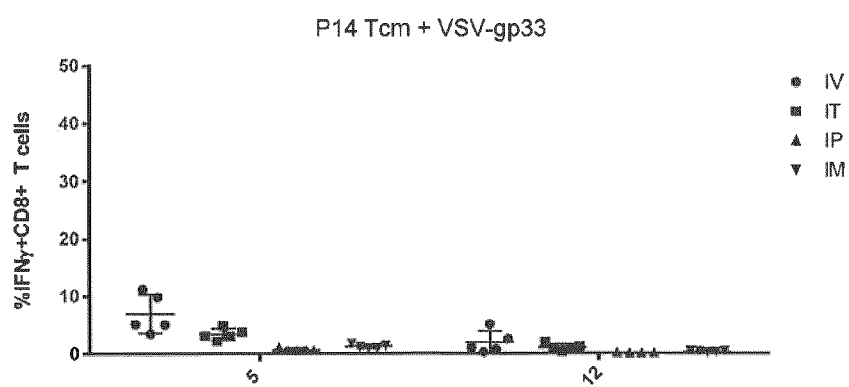
FIG. 7: Level of antigen-specific CD8+ T cell response induced by P14 Tcm ACT+OV when administered by IV, IT, IP, and IM injection. Responses are shown at 5 and 12 days post infection expressed as the % of CD8+ T cells in the peripheral circulation that produce interferon γ (IFNγ) upon stimulation with the gp33$_{33-41}$ peptide.
Figure 7:
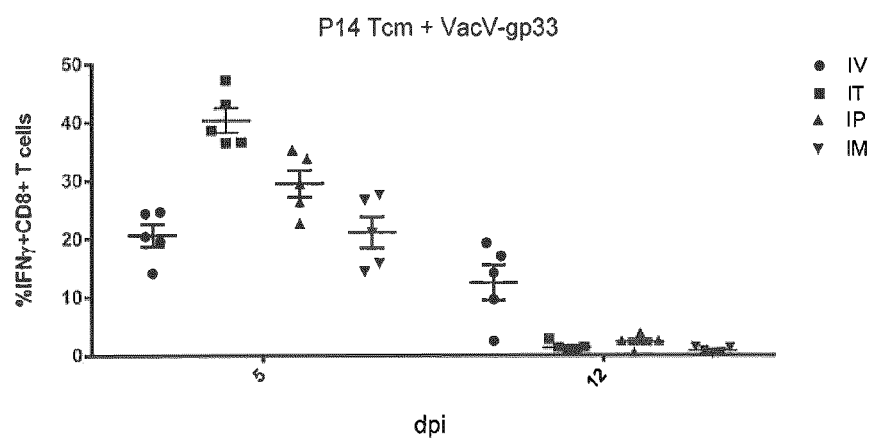

Ideally, oncolytic vaccine vectors simultaneously cause tumor debulking via direct virus infection and stimulate TAA-specific cytolytic T cells. Therefore, the route of virus injection is an important consideration when designing an oncolytic vaccine immunotherapy as the vaccine must effectively disseminate to the tumor and the lymphoid organs to achieve these two goals. In addition, the safety profile of the virus, the natural tropism of the virus, and its' ability to replicate and spread after injection must be accounted for when designing combination therapies. Therefore, we tested the ability of our combination therapy to eliminate tumors when the oncolytic vaccine was given by different routes. C57BL/6 mice were injected with $1\times10^6$ P14 Tcm cells 7 days after intradermal implantation with $1\times10^5$ B16-gp33 cells followed by intravenous (IV), intraperitoneal (IP), intratumoral (IT), or intramuscular (IM) injection with either $2\times10^8$ pfu VSV-gp33 or $7.5\times10^7$ pfu VacV-gp33 24 hours later. Tumor volumes were monitored and are shown as $mm^3$ in FIG. 5. The rhabdovirus vector (VSVgp33) was only induced effective tumor regression when given IV and showed only partial tumor regression when given by other routes (FIG. 6, left column of panels). Induction of a gp33-specific effector T cell response was measured for all injection routes used and, as was observed in the tumor regression, only the IV injection route resulted in a significant response in the P14 Tcm+VSV-gp33 treated mice (FIG. 7A). In contrast, Vaccinia based oncolytic vaccination showed more flexibility. Regardless of which route the vaccinia vaccine was administered in the context of the P14 Tcm+VacV-gp33 combination therapy complete regression of the tumor was observed in the absence of relapse (FIG. 6, right column of panels) and a significant gp33-specific CD8 T cell response was induced (FIG. 7B). Therefore, VSV administration in our combination therapy produces an effective tumor eradication response when administered IV, whereas VacV administration is flexible and leads to an effective therapeutic outcome when given IV, IT, IP and IM.

Example 5

OV Mediated Activation of P14 Tcm ACT Causes Tumor Regression in the Absence of Shared Antigen Specific Autoimmune Damage to Normal Tissue Cancerous cells are mutated and dysregulated cells derived from the host. Consequently, many of the antigenic targets of cancer cells (TAAs) are self-antigens that may also be expressed on normal cells. Careful selection of TAA targets can minimize antigen-specific collateral damage to normal tissues induced by cancer immunotherapies but unforeseen peptide cross-reactivity and normal tissue destruction has been observed in other ACT based therapies [36,37]. Therefore, the antigen-specific destruction of normal tissue juxtaposed to the complete tumor regression induced by combination therapy was evaluated.

Figure 8:
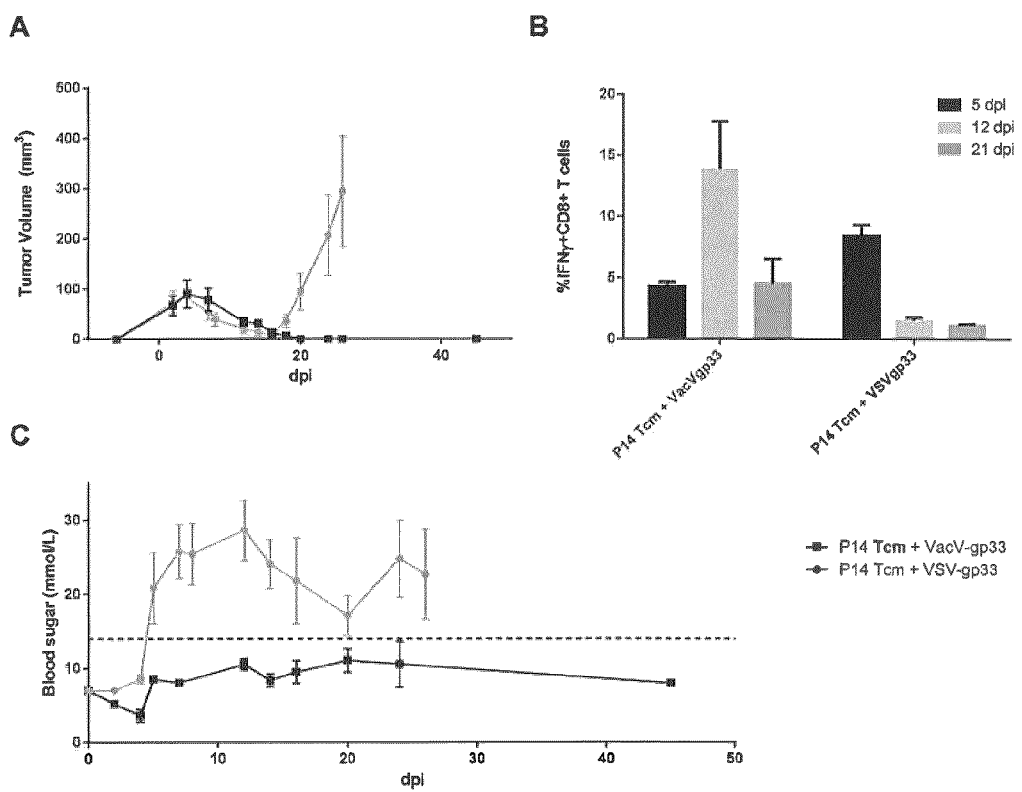
FIG. 8: Autoimmune diabetes is not induced by P14 Tcm ACT+VacV-gp33 combination therapy despite showing similar tumor regression kinetics and peak T cell response level as P14 Tcm ACT+VSV-gp33 treatment. Tumor volume was measured using calipers and expressed as mm$^3$ at each indicated day post infection (dpi) with 0 dpi representing the day of oncolytic virus injection (A). Responses at 5, 12 and 21 days post infection are expressed as the % of CD8+ T cells in the peripheral circulation that produce interferon γ (IFNγ) upon stimulation with the gp33 peptide (B). Blood sugar levels were monitored with a blood glucose meter and expressed as mmol/L at each indicated day post infection (dpi) with 0 dpi representing the day of oncolytic virus injection (C).

RIPgp mice bearing a B16-gp33 tumor were used to determine antigen-specific autoimmunity induced by the combination P14 Tcm ACT and OV therapies. RIPgp mice are a transgenic strain that expresses the LCMV glycoprotein, containing the gp33 peptide, selectively in the pancreatic beta cells. Therefore, a cytolytic immune response against gp33 in these mice can cause both tumor and pancreatic beta cell destruction resulting in tumor regression and diabetes respectively. RIP-gp mice were injected with $1\times10^6$ P14 Tcm cells 7 days after intradermal implantation with $1\times10^5$ B16-gp33 cells followed by intravenous injection 24 hours later with either $2\times10^8$ pfu VSV-gp33 or $7.5\times10^7$ pfu VacV-gp33. The tumor regression after treatment with either virus was monitored. Tumor volume peaked at five days post infection at about 100 $mm^3$ for both virus treatments and steadily declined thereafter (FIG. 8A). The rate of VSV-gp33 induced tumor regression was slightly quicker than that of VacV-gp33 but ultimately P14 Tcm+VacV-gp33 treated tumors completely regressed and did not relapse whereas P14 Tcm+VSV-gp33 treated tumors failed to completely regress before relapsing (FIG. 8A).

Figure 9:
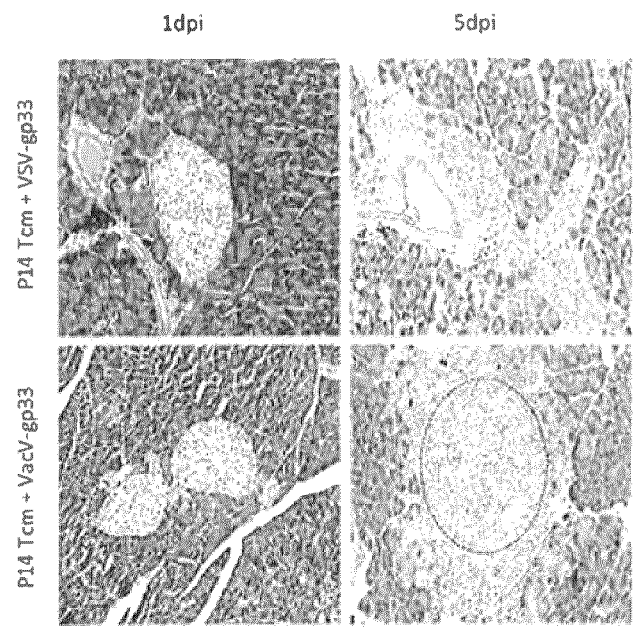
FIG. 9: Pancreatic beta cell destruction induced in P14 Tcm+VSV-gp33 treated RIPgp mice but not in P14 Tcm+VacV-gp33 treated RIPgp mice despite evidence of immune cell infiltration. Pancreatic tissue sections taken at 1 and 5 dpi stained with hematoxylin and eosin (A) or insulin immunohistochemistry (B) are shown.
Figure 9:
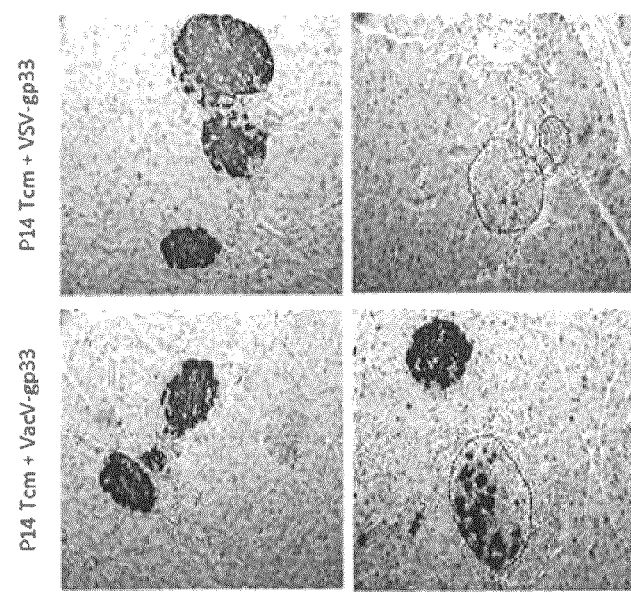

Blood sugar levels of treated mice were monitored using a blood glucometer in order to detect diabetes induction. For these experiments, diabetes was defined as a blood sugar above 14 mmol/L (shown as a dotted line in FIG. 8C). Diabetes was induced at day five post infection in the VSV-gp33 treated mice (FIG. 8C), which correlates with the peak immune response induced by this therapy. Disruption of the pancreatic islet structure was observed in hematoxylin and eosin stained pancreas tissues taken from mice at day five post treatment with VSV-gp33 (FIG. 9A). Immunohistochemistry probing for insulin protein performed on the same tissues showed a dramatic decrease in the number of insulin positive cells in the islets of (FIG. 9B) indicating that the insulin producing beta cells have been destroyed in these mice. Since the gp33 peptide is specifically expressed in the beta cells of RIP-gp mice, it appears that the P14 Tcm ACT induced antigen-specific damage of normal tissues when combined with VSV. In contrast, mice treated with P14 Tcm+VacVgp33 combination therapy did not become diabetic (FIG. 8C) at any time point after treatment despite showing an equivalent peak gp33-specific T cell response (FIG. 8B). Pancreas tissues from these mice showed enlarged islets at day five post infection (FIG. 8A) due to significant infiltration of insulin negative cells (FIG. 9B) into the islets. Insulin positive cells were still observed at high numbers in the islet so it appears that the infiltrating cells did not exhibit effective, if any, beta cell gp33-specific cytolytic activity. Both VacV-gp33 and VSV-gp33 induced an equivalent peak gp33-specific response so the difference in autoimmune damage between the oncolytic vaccines cannot be attributed to the magnitude of response induced, but rather the quality of the stimulated T cells. Therefore, combination of P14 Tcm ACT with either of the tested oncolytic vaccines is able to induce tumor regression but VSV-gp33 induces collateral antigen-specific damage of normal tissue whereas VacV-gp33 does not in the same system.

Example 6

Programming Human T Cells with Antigen Presenting Cells, IL21, IL15, and Rapamycin Selectively Enriches Antigen Specific Tcm Cells Human antigen-specific CD8 T cells can be enriched and "programmed" (guided differentiation) into a central memory phenotype in the presence of antigen pulsed autologous dendritic cells, IL21, IL17, and IL2 [21]. The initial programming is followed by a cell-sorting step to purify the population for the desired type of T cells (typically by tetramer staining) and then expansion of this purified population by culturing the T cells in the presence of anti-CD3/CD28 antibodies and IL2 (a rapid expansion protocol termed REP). Although this method can produce very high levels of the desired T cells, it is time consuming, requires expensive equipment. In contrast, programming/enrichment by co-culturing lymphocytes with dendritic cells in the presence of antigen, IL21, IL15 and rapamycin selectively enriches the Tcm cells present in the original T cell population without necessitating cell sorting prior to subsequent expansion (REP).

To demonstrate this, aliquoted human PBMCs from the same source were co-cultured with dendritic cells (DCs) pulsed with pp65 (a human cytomegalovirus (HCMV) derived immuno-dominant peptide) following either the method described in U.S. Patent Application Publication No.

Figure 10:
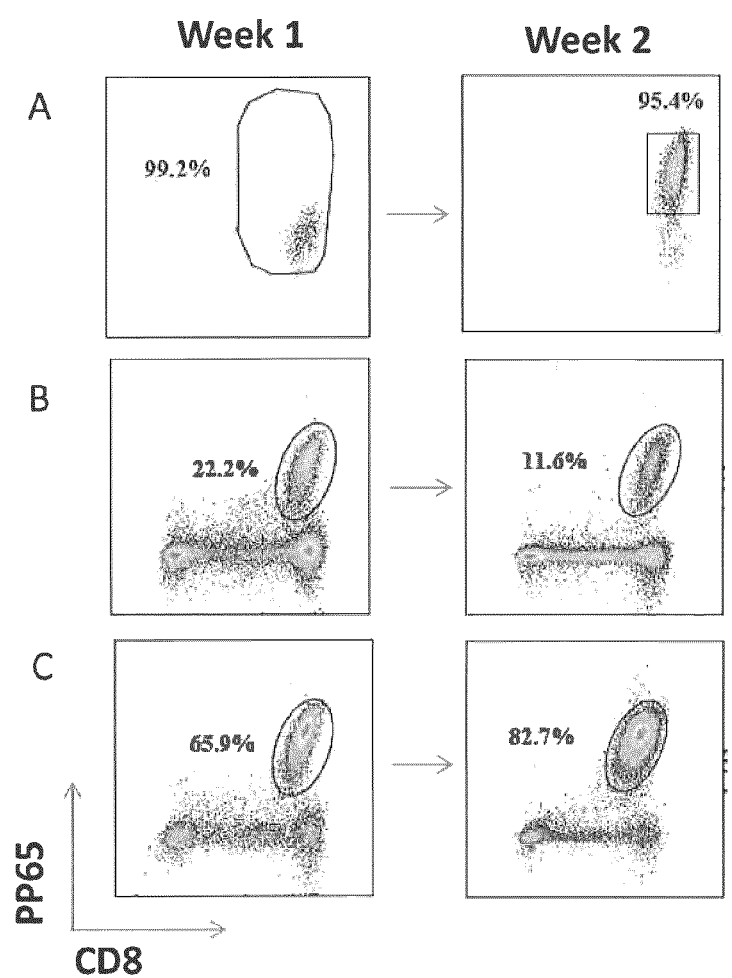
FIG. 10: Expansion of programmed T cells with IL21, IL15, and rapamycin produces high levels of pp65-specific CD8+ T cells without cell sorting. Aliquoted human T-cells from PBMCs from the same source were cultured for two weeks by the method of Yee, involving co-culture with dendritic cells, IL21, IL7, and IL2 (A and B), or co-culture with dendritic cells, IL21, IL15, and rapamycin (C). After two weeks of such enrichment/programming the cells in each co-culture were either sorted using pp65 tetramer staining and expanded with anti-CD3/CD28 Abs and IL2 (A), or expanded directly with anti-CD3/CD28 Abs and IL2 without prior sorting (B and C). After 1 week and 2 weeks of expansion, the overall level of the desired pp65-specific CD8+ T cells within each culture was determined.

2015/0023938 (30 ng/mL IL-21 for the first week and then adding 10 ng/mL IL-2 and 5 ng/mL IL-7 for the second week) or the IL21, IL15, rapamycin method described herein to enrich and program pp65-specific CD8+ T cells. Briefly, CD25-depleted PMBCs were co-cultured for two weeks with irradiated peptide-loaded DCs and IL21, IL15 and rapamycin and one week with IL21, IL15 and rapamycin only (no peptide-loaded DCs) (defined as phase I: enrichment and programming) followed by expansion for two weeks with IL2 and CD3/CD28 antibodies (defined as phase II: rapid expansion or REP) without an intervening sorting step. The enrichment/programming method described in U.S. Patent Application Publication 2015/0023938 can produce a T cell population with >99% antigen specific T cells after 1 week of expansion falling to about 95% after 2 weeks of expansion, if the enriched programmed cells are sorted with a cell sorter prior to REP (FIG. 10A). The same method without cell sorting produces a T cell population with about 22% antigen specific T cells after 1 week of expansion which falls to <12% after 2 weeks of expansion (FIG. 10B). In contrast, the method described here utilizing IL21, IL15 and rapamycin yields a T cell population with about 66% antigen specific T cells after 1 week of expansion rising to >82% after 2 weeks of expansion (FIG. 10C). Thus, the IL21, IL15, rapamycin programming/enrichment step not only produces a population of T cells that is highly enriched for central memory T cells, but these cells are better able to tolerate the stress of prolonged exposure to anti-CD3/CD28 Abs and IL2 in the course of REP.

Together these results indicate that a therapeutically effective amount of human Tcm cells can be prepared for ACT without requiring the time and expense of cell sorting. Further, the results indicate that the trade-off inherent to anti-CD3/CD28 Abs-mediated expansion between higher numbers of T cells at lower potency is shifted in favor of higher potency Tcm cells when the cells are programmed and enriched with IL21, IL15, and rapamycin.

Example 7

Tumor Eradication with ACT+OV Combination Therapy does not Require Prior Lymphodepletion The effect of prior lymphodepletion on the ability of the combination ACT+OV therapy to eradicate tumors was tested using BALB/c (as wild type) and BALB/c-NRG mice, wherein the BALB/c-NRG mice lack any endogenous lymphocytes at all due to Rag1KO (Cg-Rag1$^{tm1Mom}$) and IL2RγcKO (Il2rg$^{tm1Wjl}$) knockout mutations. Both BALB/c and BALB/c-NRG mice were injected with CMS5 cells and tumors were allowed to develop for 6 days. Mice were then injected with DUC18 Tcm ACT cells as indicated, followed one day later by injection of recombinant Maraba virus constructs as indicated, and tumor volumes of the subject mice followed for 5 to 6 weeks.

Figure 11:
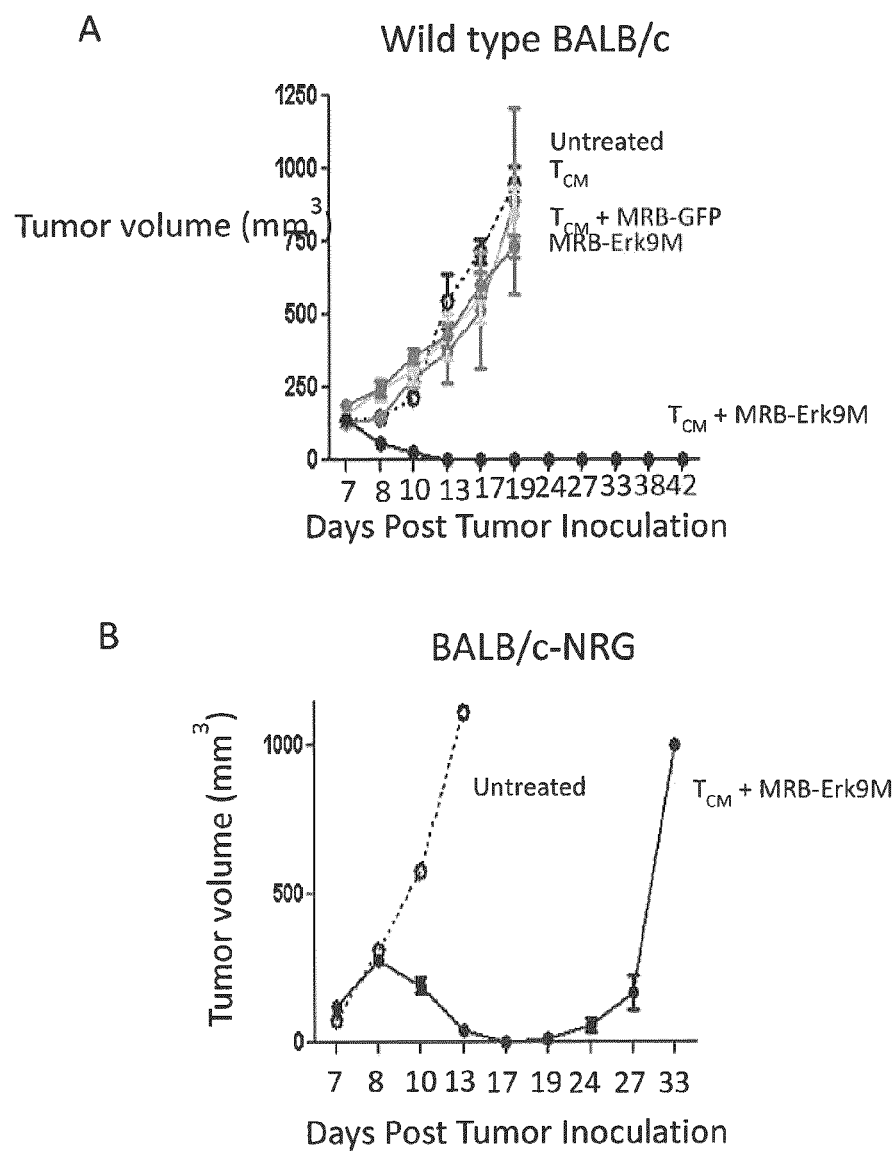
FIG. 11: Lymphodepletion is not necessary for establishing an effective ACT+OV response. Established CMS5 tumors can be cured by DUC18 transgenic T cells+Maraba-Erk9M in wild-type Balb/c mice without ablation of host lymphocytes (A). However, Balb/c-NRG mice lacking any endogenous lymphocytes fail to clear the tumors entirely, undergoing an initial phase of partial tumor clearance only to relapse (B).

As expected the untreated BALB/c mice, as well as BALB/c mice receiving only ACT alone or only OV treatment showed no tumor control and tumor volume grew rapidly (FIG. 11A, Tcm and MRB-Erk9m respectively). In addition, combination therapy comprising DUC18 Tcm ACT and OV treatment with a recombinant Maraba-GFP construct also failed to affect tumor growth in these mice (FIG. 11A, Tcm+MRB-GFP). In contrast, combination therapy with DUC18 Tcm ACT and OV treatment with recombinant Maraba-Erk9M completely eradicated tumors, indicating that both Tcm and an OV vector expressing the specific antigen are required for complete tumor eradication.

Surprisingly, BALB/c-NRG mice behaved somewhat differently. In this case, the identical combination of DUC18 Tcm ACT and OV Maraba-Erk9M treatment only produced transient tumor regression and after 2-3 weeks the tumors relapsed (FIG. 11B). Without being bound to theory, this may indicate that endogenous T cells are required to cooperate with transferred (ACT) T cells for complete tumor eradication or mediate rejection of antigen-lost variants via epitope spreading involving endogenous T cells targeting other tumor antigens.

Figure 12:
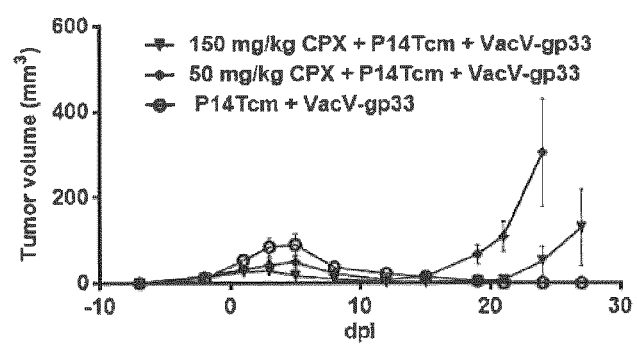
FIG. 12: Cyclophosphamide lymphodepletion is detrimental for anti-tumor effect of Tcm ACT+OV therapy. Combination treatment with P14 Tcm+VacV-gp33 of established B16-gp33 tumors with or without prior ablation of host lymphocytes via cyclophosphamide treatment at low (50 mg/kg) a high doses (150 mg/kg) are shown (A). Tumor volume was measured using calipers and expressed as mm$^3$ at each indicated day post infection (dpi) with 0 dpi representing the day of oncolytic virus injection. Responses at 5, 12 and 21 days post infection are shown expressed as the % of CD8+ T cells in the peripheral circulation that produce interferon γ (IFNγ) upon stimulation with the gp33 peptide (B).
Figure 12:
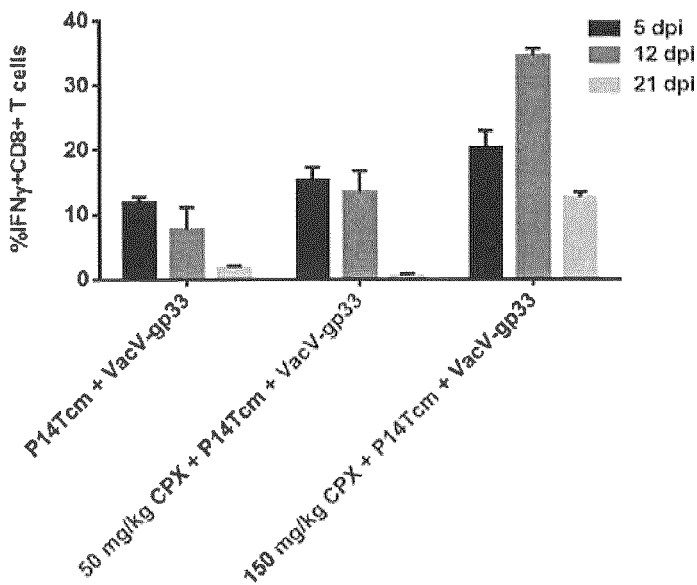

The consequence of chemical induced lymphodepletion pretreatment on Tcm+ACT, C57BL/6 mice was also tested. Mice bearing B16-gp33 tumors were treated with P14 Tcm+VacV-gp33 with or without prior lymphodepletion induced by CPX treatment. Mice treated with P14 Tcm+VacV-gp33 in the absence of CPX pretreatment showed complete tumor regression (FIG. 12A) and a peak response of ~12% IFNγ+CD8 T cell response at 12 days post infection. In contrast, mice pretreated with low dose (50 mg/kg) and high dose (150 mg/kg) CPX where unable to completely regress the tumor, eventually succumbing to tumor relapse (FIG. 12A). The lack of tumor control in CPX treated mice had no correlation with the magnitude of gp33-specific CD8 T cell responses as these mice developed responses of equivalent or greater magnitude compared to mice that were not treated with the drug (FIG. 12B). Therefore, chemical lymphodepletion does not enhance the anti-tumor effect induced by the combination therapy. Indeed, CPX treatment appears to have a detrimental effect on the anti-tumor activity of antigen-specific CD8+ T cell response induced by Tcm ACT+OV combination therapy.

These results not only demonstrate that the combination of ACT+OV treatment described here can bypass preconditioning lymphodepletion or lymphoablation, but that lymphodepletion/lymphoablation may be detrimental to the overall efficacy of the therapy.

Different embodiments of the invention are shown by the above examples. Those skilled in the art could develop alternatives to the methods mentioned above that are within the scope of the invention and defined claims.

All publications, patents and patent applications are herein incorporated by reference in their entirety to the same extent as if each individual publication, patent, or patent application was specifically and individually indicated as incorporated by reference in its entirety. Where a term in the present application is defined differently in a document incorporated herein by reference, the definition provided herein is to serve as the definition for the term.

REFERENCES

1. Minniti G, Sanctis V, Muni R, Filippone F, Bozzao A, Valeriani M, et al. Radiotherapy plus concomitant and adjuvant temozolomide for glioblastoma in elderly patients. J. Neurooncol. 2008 88:97-103.
2. Mellman I, Coukos G, Dranoff G. Cancer immunotherapy comes of age. Nature 2011 480:480-9.
3. Ahmadzadeh M, Johnson L A, Heemskerk B, Wunderlich J R, Dudley M E, White D E, et al. Tumor antigen-specific CD8 T cells infiltrating the tumor express high levels of PD-1 and are functionally impaired. Blood. 2009 114:1537-44.
4. Rabinovich G A, Gabrilovich D, Sotomayor E M. Immunosuppressive Strategies that are Mediated by Tumor Cells. Annu. Rev. Immunol. 2007 25:267-96.

5. Kim R, Emi M, Tanabe K, Arihiro K. Tumor-driven evolution of immunosuppressive networks during malignant progression. Cancer Res. 2006 66:5527-36.
6. Mahoney K M, Freeman G J, McDermott D F. The Next Immune-Checkpoint Inhibitors: PD-1/PD-L1 Blockade in Melanoma. Clin. Ther. 2015 37:764-82.
7. Leach D R, Krummel M F, Allison J P. Enhancement of antitumor immunity by CTLA-4 blockade. Science. 1996 271:1734-6.
8. Camacho L H. CTLA-4 blockade with ipilimumab: biology, safety, efficacy, and future considerations. Cancer Med. 2015 4:661-72.
9. Zamarin D, Holmgaard R B, Subudhi S K, Park J S, Mansour M, Palese P, et al. Localized oncolytic virotherapy overcomes systemic tumor resistance to immune checkpoint blockade immunotherapy. Sci. Transl. Med. 2014 6:226-32.
10. Winograd R, Byrne K T, Evans R A, Odorizzi P M, Meyer A R L, Bajor D L, et al. Induction of T-cell Immunity Overcomes Complete Resistance to PD-1 and CTLA-4 Blockade and Improves Survival in Pancreatic Carcinoma. Cancer Immunol. Res. 2015 3:399-411.
11. Restifo N P, Dudley M E, Rosenberg S A. Adoptive immunotherapy for cancer: harnessing the T cell response. Nat. Rev. Immunol. 2012. 12:269-81.
12. Rapoport A P, Stadtmauer E A, Binder-Scholl G K, Goloubeva O, Vogl D T, Lacey S F, et al. NY-ESO-1-specific TCR-engineered T cells mediate sustained antigen-specific antitumor effects in myeloma. Nat. Med. 2015 21:1-20.
13. Nakazawa Y, Huye L E, Salsman V S, Leen A M, Ahmed N, Rollins L, et al. PiggyBac-mediated cancer immunotherapy using EBV-specific cytotoxic T-cells expressing HER2-specific chimeric antigen receptor. Mol. Ther. 2011 19:2133-43.
14. Stevanović S, Draper L M, Langhan M M, Campbell T E, Kwong M L, Wunderlich J R, et al. Complete regression of metastatic cervical cancer after treatment with human papillomavirus-targeted tumor-infiltrating T cells. J. Clin. Oncol. 2015 33:1543-50.
15. Klebanoff C A, Gattinoni L, Torabi-Parizi P, Kerstann K, Cardones A R, Finkelstein S E, et al. Central memory self/tumor-reactive CD8+ T cells confer superior antitumor immunity compared with effector memory T cells. Proc. Natl. Acad. Sci. U.S.A 2005 102:9571-6.
16. Topalian S L, Muul L M, Solomon D, Rosenberg S A. Expansion of human tumor infiltrating lymphocytes for use in immunotherapy trials. J. Immunol. Methods 1987 102:127-41.
17. Dudley M E, Yang J C, Sherry R, Hughes M S, Royal R, Kammula U, et al. Adoptive cell therapy for patients with metastatic melanoma: Evaluation of intensive myeloablative chemoradiation preparative regimens. J. Clin. Oncol. 2008; 26:5233-9.
18. Ram R, Storb R, Sandmaier B M, Maloney D G, Woolfrey A, Flowers MED, et al. Non-myeloablative conditioning with allogeneic hematopoietic cell transplantation for the treatment of high-risk acute lymphoblastic leukemia. Haematologica. 2011 96:1113-20.
19. Topalian S L, Solomon D, Avis F P, Chang A E, Freerksen D L, Linehan W M, et al. Immunotherapy of patients with advanced cancer using tumor-infiltrating lymphocytes and recombinant interleukin-2: a pilot study. J Clin Oncol 1988 6:839-53.
20. Chapuis A G, Thompson J A, Margolin K A, Rodmyre R, Lai I P, Dowdy K, et al. Transferred melanoma-specific CD8+ T cells persist, mediate tumor regression, and acquire central memory phenotype. Proc. Natl. Acad. Sci. 2012 109:4592-7.
21. Pollack S M, Jones R L, Farrar E a, Lai I P, Lee S M, Cao J, et al. Tetramer guided, cell sorter assisted production of clinical grade autologous NY-ESO-1 specific CD8(+) T cells. J. Immunother. Cancer 2014 2:36.
22. Zhang L, Bridle B W, Chen L, Pol J, Spaner D, Boudreau J E, et al. Delivery of viral-vectored vaccines by B cells represents a novel strategy to accelerate CD8(+) T-cell recall responses. Blood. 2013 121:2432-9.
23. Oldstone M B, Tishon A, Eddleston M, de la Torre J C, McKee T, Whitton J L. Vaccination to prevent persistent viral infection. J. Virol. 1993 67:4372-8.
24. Pol J G, Zhang L, Bridle B W, Stephenson K B, Rességuier J, Hanson S, et al. Maraba virus as a potent oncolytic vaccine vector. Mol. Ther. 2014 22:420-9.
25. Boudreau J E, Bridle B W, Stephenson K B, Jenkins K M, Brunellière J, Bramson J L, et al. Recombinant vesicular stomatitis virus transduction of dendritic cells enhances their ability to prime innate and adaptive antitumor immunity. Mol. Ther. 2009 17:1465-72.
26. Brun J, McManus D, Lefebvre C, Hu K, Falls T, Atkins H, et al. Identification of genetically modified Maraba virus as an oncolytic rhabdovirus. Mol. Ther. 2010 18:1440-9.
27. Rochman Y, Spolski R, Leonard W J. New insights into the regulation of T cells by gamma(c) family cytokines. Nat. Rev. Immunol. 2009 9:480-90.
28. Crawley A M, Katz T, Parato K, Angel J B. IL-2 receptor gamma chain cytokines differentially regulate human CD8+CD127+ and CD8+CD127− T cell division and susceptibility to apoptosis. Int. Immunol. 2009 21:29-42.
29. Dudley M E, Wunderlich J R, Shelton T E, Even J, Rosenberg S A. Generation of tumor-infiltrating lymphocyte cultures for use in adoptive transfer therapy for melanoma patients. J. Immunother. 2003 26:332-42.
30. Hinrichs C S, Spolski R, Paulos C M, Gattinoni L, Kerstann K W, Palmer D C, et al. IL-2 and IL-21 confer opposing differentiation programs to CD8+ T cells for adoptive immunotherapy. Blood 2008 111:5326-33.
31. Schluns K S, Lefrançois L. Cytokine control of memory T-cell development and survival. Nat. Rev. Immunol, 2003 3:269-79.
32. Zeng R, Spolski R, Finkelstein S E, Oh S, Kovanen P E, Hinrichs C S, et al. Synergy of IL-21 and IL-15 in regulating CD8+ T cell expansion and function. J. Exp. Med. 2005 201:139-48.
33. Araki K, Turner A P, Shaffer V O, Gangappa S, Keller S a, Bachmann M F, et al. mTOR regulates memory CD8 T-cell differentiation. Nature. 2009 460:108-12.
34. Rao R R, Li Q, Odunsi K, Shrikant P A. The mTOR Kinase Determines Effector versus Memory CD8+ T Cell Fate by Regulating the Expression of Transcription Factors T-bet and Eomesodermin. Immunity. 2010 32:67-78.
35. Li Q, Rao R, Vazzana J, Goedegebuure P, Odunsi K, Gillanders W, et al. Regulating mammalian target of rapamycin to tune vaccination-induced CD8(+) T cell responses for tumor immunity. J. Immunol. 2012 188: 3080-7.
36. Cameron B J, Gerry A B, Dukes J, Harper J V, Kannan V, Bianchi F C, et al. Identification of a Titin-derived HLA-A1-presented peptide as a cross-reactive target for engineered MAGE A3-directed T cells. Sci. Transl. Med. 2013 5:197ra103.
37. Chinnasamy N, Wargo J a, Yu Z, Rao M, Frankel T L, Riley J P, et al. A TCR targeting the HLA-A*0201- restricted epitope of MAGE-A3 recognizes multiple epitopes of the MAGE-A antigen superfamily in several types of cancer. J. Immunol. 2011 186:685-96.

The invention claimed is:

1. A method for treating cancer in a subject in need thereof comprising the steps of:
   (i) administering to the subject an adoptive cell therapeutic (ACT) comprising a population of CD8+ T cells wherein at least about 50% of the CD8+ T cells display a central memory phenotype and are specific for a tumor antigen expressed by the cancer, and wherein the population of CD8+ T cells is prepared by ex vivo culture of PBMCs or TILs in the presence of the tumor antigen, APCs and a composition comprising or consisting essentially of IL21, IL15, and rapamycin; and
   (ii) subsequently administering to the subject a replicative oncolytic virus (OV) vaccine expressing the tumor antigen.

2. The method of claim 1, wherein the ex vivo culture of PBMCs or TILs is followed by ex vivo culture of the PBMCs or TILs in a composition comprising or consisting essentially of IL21, IL15, and rapamycin and in the absence of the tumor antigen and APCs to enrich and program antigen specific CD8+ T cells.

3. The method of claim 1, wherein the composition comprising or consisting essentially of IL21, IL15 and rapamycin does not comprise IL2.

4. The method of claim 1, wherein the population of CD8+ T cells is produced by transducing PBMCs with recombinant T cell receptor (TCR) or CAR specific for the tumor antigen and culturing the transduced PBMCs ex vivo.

5. The method of claim 1, wherein the population of CD8+ T cells is produced by ex vivo culture of CD25-depleted PBMCs.

6. The method of claim 1, wherein IL21 and IL15 are present at a concentration of about 1 ng/ml to about 20 ng/ml and rapamycin is present at a concentration of from about 10 ng/ml to about 30 ng/ml.

7. The method of claim 1, wherein ex vivo culture of the PBMCs or TILs for antigen-specific T cell enrichment and programming is followed by ex vivo expansion of the cells in culture, wherein a T cell purification step is not performed after ex vivo culture.

8. The method of claim 1, wherein the subject is not administered IL2.

9. The method of claim 1, wherein the replicative oncolytic virus is a rhabdovirus.

10. The method of claim 9, wherein the rhabdovirus is a recombinant or wild type Maraba virus or a recombinant or wild type VSV.

11. The method of claim 9, wherein the rhabdovirus is administered intravascularly to the subject.

12. The method of claim 1, wherein the replicative oncolytic virus is a wild type or recombinant vaccinia virus.

13. The method of claim 12, wherein the vaccinia virus is a Wyeth, Western Reserve or Copenhagen strain.

14. The method of claim 12, wherein the vaccinia virus is administered intravascularly, intratumorally, intramuscularly, or intraperitoneally.

15. The method of claim 1, wherein the OV is administered to the subject about one hour to about 31 days after the ACT therapy.

16. The method of claim 1, wherein the subject does not undergo lymphodepletion prior to receiving the ACT.

17. The method of claim 1, wherein the tumor antigen is selected from the group consisting of alphafetoprotein (AFP), carcinoembryonic antigen (CEA), CA 125, Her2, dopachrome tautomerase (DCT), GP100, Melan-A/MART-1, MAGE proteins, BAGE proteins, GAGE proteins, NY-ESO1, WT-1, survivin, tyrosinase, SSX2, Cyclin-A1, KIF20A, MUC5AC, Meloe, Lengsin, Kallikrein 4, IGF2B3, glypican-3, HPV E6 and HPV E7.

18. The method of claim 1, wherein the cancer is selected from the group consisting of melanoma, sarcoma, lymphoma, carcinoma, brain cancer, breast cancer, liver cancer, lung cancer, kidney cancer, pancreatic cancer, esophageal cancer, stomach cancer, colon cancer, colorectal cancer, bladder cancer, prostate cancer and leukemia.

19. The method of claim 1, wherein the cancer is a solid tumor.

20. The method of claim 1, wherein the cancer is a metastasis.

21. The method of claim 1, wherein the tumor antigen is a tumor-specific antigen.

22. The method of claim 1, wherein the tumor antigen is a self-antigen.

23. The method of claim 1, wherein the OV is administered to the subject multiple times following administration of the ACT.

24. The method of claim 1, wherein the subject is administered at least a first combination therapy and a second combination therapy, wherein the tumor antigen is the same for the first and second combination therapy.

25. The method of claim 1, wherein the subject is administered at least a first combination therapy and a second combination therapy, wherein the tumor antigen is not the same for the first and second combination therapy.

26. The method of claim 1, wherein the population of CD8+ T cells is autologous to the subject.

27. The method of claim 1, wherein the subject is a human.

28. The method of claim 1, wherein the antigen presenting cell is a dendritic cell.

29. The method of claim 1, wherein the tumor antigen and antigen presenting cell are present in the form of tumor antigen peptide-loaded antigen presenting cells.

30. The method of claim 29, wherein the tumor antigen peptide-loaded antigen presenting cells are obtained by
  (i) culturing adherent PBMCs from the subject with GM-CSF and IL-4 to obtain autologous dendritic cells, optionally followed by stimulation of the dendritic cells with TNFα, IL-1b, IL-6, PGE-2, IL-4 and GM-CSF;
  (ii) pulsing the dendritic cells with tumor antigen peptide; and
  (iii) irradiating the tumor antigen peptide loaded dendritic cells.

31. The method of claim 1, wherein the tumor antigen is present in the composition in the form of tumor material from the subject.

32. A method for preparing a population of tumor antigen-specific human CD8+ T cells with a central memory phenotype comprising
  (i) culturing peripheral blood mononuclear cells (PBMCs) or tumor infiltrating lymphocytes (TILs) obtained from a human ex vivo in the presence of a tumor antigen, APCs, and a composition comprising or consisting essentially of IL15, IL21 and rapamycin and which does not comprise IL2, to obtain a population of tumor antigen-specific human CD8+ T cells with a central memory phenotype; and
  (ii) expanding the obtained CD8+ T cells.

33. The method of claim 32, wherein the method does not comprise a T cell purification step between steps (i) and (ii).

34. The method of claim 32, wherein the PBMCs are obtained from a human with cancer.

35. The method of claim 32, wherein CD25+ cells are depleted from the PBMCs before the PBMCs are cultured ex vivo.

36. The method of claim 32, comprising
  (i) transducing PBMCs or TILs obtained from a human cancer subject with a recombinant TCR or CAR specific for a tumor antigen expressed by the PBMCs or TILs;
  (ii) culturing the transduced PBMCs or TILs in culture medium in the presence of the tumor antigen, APCs and a composition comprising or consisting essentially of IL15, IL21 and rapamycin and which does not comprise IL2, to obtain a population of human CD8+ T cells with a central memory phenotype; and
  (iii) expanding the obtained CD8+ T cells in culture.

37. The method of claim 32, further comprising a step of administering the obtained population of human CD8+ T cells to the subject.

38. The method of claim 32, wherein expanding the obtained CD8+ T cells comprises expanding the obtained CD8+ T cells in a culture medium comprising anti-CD3 and anti-CD28 antibodies and IL2.

* * * * *

```
                           SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Lymphocytic choriomeningitis virus gp33 epitope
      LCMV-gp33-41

<400> SEQUENCE: 1

Lys Ala Val Tyr Asn Phe Ala Thr Met
1               5

<210> SEQ ID NO 2
<211> LENGTH: 9
<212> TYPE: PRT
<213> ORGANISM: Artificial Sequence
<220> FEATURE:
<223> OTHER INFORMATION: Dopachrome tautomerase (DCT) epitope DCT180-188

<400> SEQUENCE: 2

Ser Val Tyr Asp Phe Phe Val Trp Leu
1               5

<210> SEQ ID NO 3
<211> LENGTH: 9
<212> TYPE: PRT
<213> ORGANISM: Artificial Sequence
<220> FEATURE:
<223> OTHER INFORMATION: CMS5 fibrosarcoma rejection antigen mutated
      ERK2 (MAPK1) epitope Erk9M136-144

<400> SEQUENCE: 3

Gln Tyr Ile His Ser Ala Asn Val Leu
1               5
```